United States Patent
Yu

(10) Patent No.: US 10,265,518 B2
(45) Date of Patent: *Apr. 23, 2019

(54) CRANIOFACIAL NEUROSTIMULATION FOR TREATMENT OF PAIN CONDITIONS

(71) Applicant: Steven Sounyoung Yu, Fairfax, VA (US)

(72) Inventor: Steven Sounyoung Yu, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/589,949

(22) Filed: May 8, 2017

(65) Prior Publication Data
US 2017/0239461 A1  Aug. 24, 2017

Related U.S. Application Data

(63) Continuation of application No. 14/937,816, filed on Nov. 10, 2015, now Pat. No. 9,643,003.

(51) Int. Cl.
*A61N 1/00* (2006.01)
*A61N 1/05* (2006.01)
*A61N 1/36* (2006.01)

(52) U.S. Cl.
CPC ......... *A61N 1/0553* (2013.01); *A61N 1/0526* (2013.01); *A61N 1/0558* (2013.01); *A61N 1/36071* (2013.01); *A61N 1/36075* (2013.01); *A61N 1/36185* (2013.01)

(58) Field of Classification Search
CPC ................ A61N 1/0553; A61N 1/0558; A61N 1/36185; A61N 1/36071; A61N 1/36075; A61N 1/0526; A61N 1/3605; A61N 1/36062
See application file for complete search history.

(56) References Cited

U.S. PATENT DOCUMENTS

| | | | |
|---|---|---|---|
| 9,789,307 B2 * | 10/2017 | Gerber | A61N 1/36 |
| 2009/0112282 A1 * | 4/2009 | Kast | A61N 1/0553 607/46 |
| 2013/0238076 A1 * | 9/2013 | Feler | A61N 1/0553 607/148 |
| 2017/0151432 A1 * | 6/2017 | Christopherson | A61N 1/3601 |

* cited by examiner

*Primary Examiner* — Scott M. Getzow

(57) ABSTRACT

Electrical neurostimulation leads for use in craniofacial peripheral nerve neurostimulation (e.g. occipital neurostimulation). Paddle leads, lead wires, lead wire anchors, tools, or other hardware can be designed for implantation in the craniofacial region. This can address problems of electrical neurostimulation in the craniofacial region such as lead migration, hardware breakage, patient discomfort, or other problems.

20 Claims, 25 Drawing Sheets

FIG. 8A
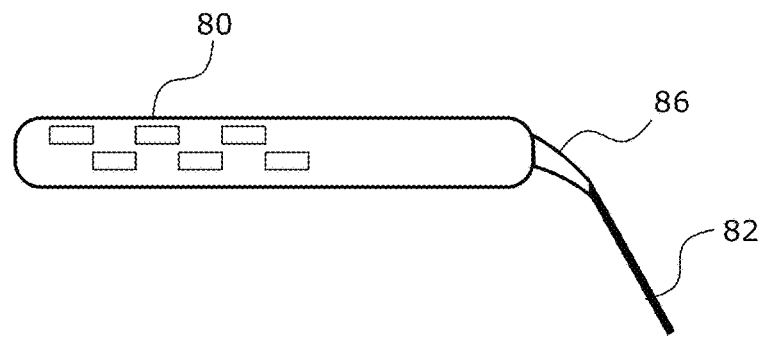
FIG. 8B
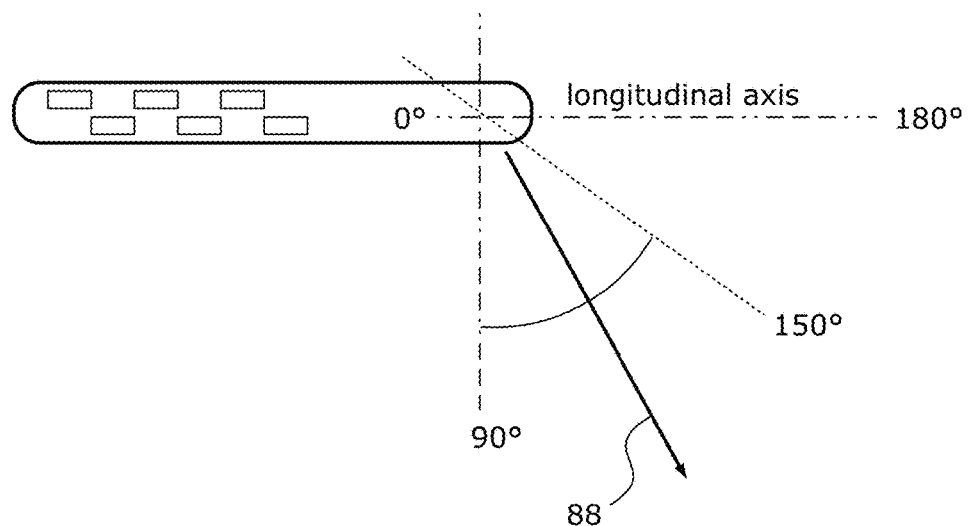
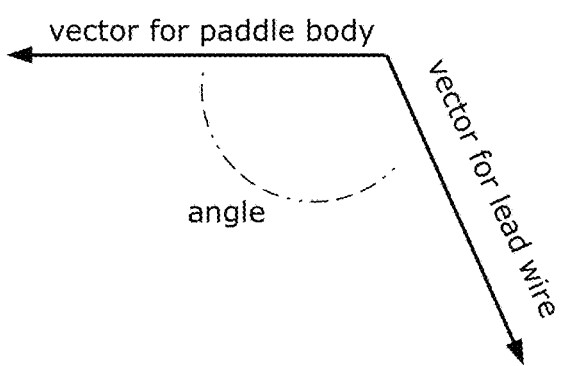

caudal direction

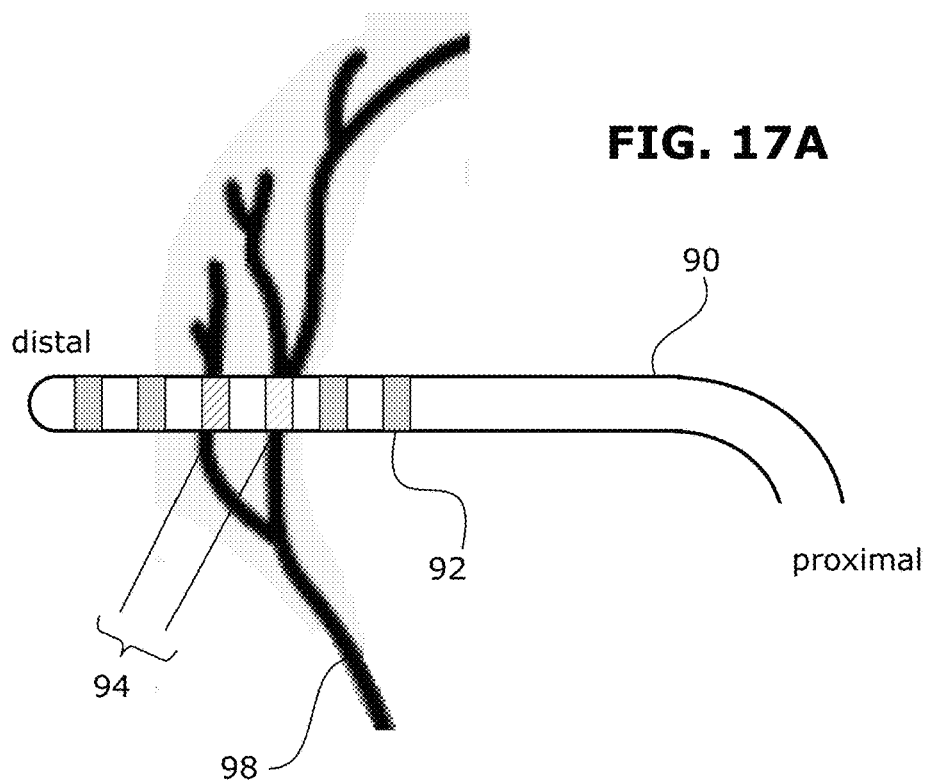
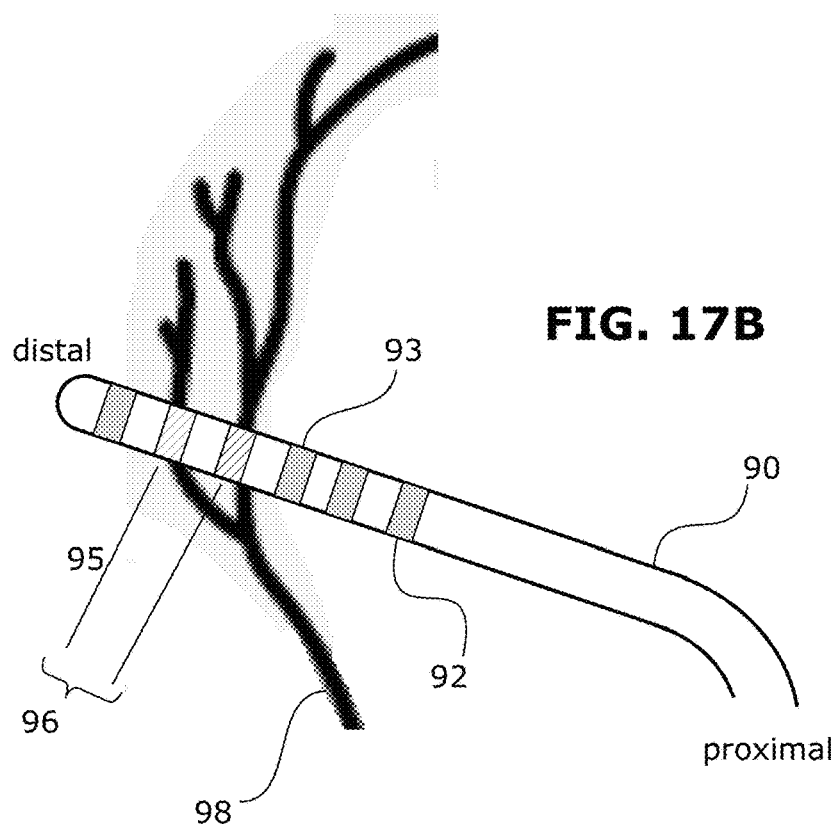

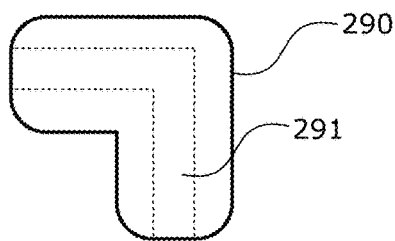
FIG. 24A
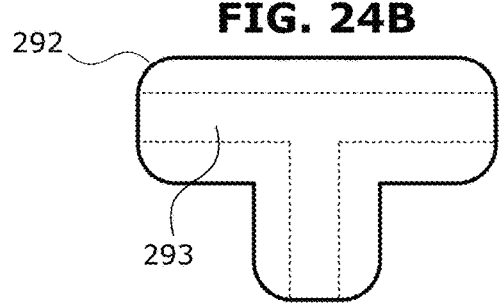
FIG. 24B
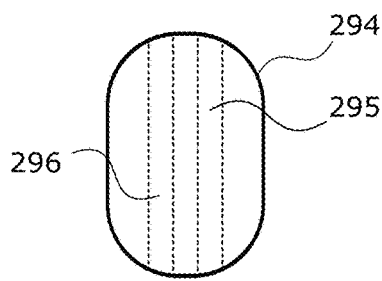
FIG. 24C
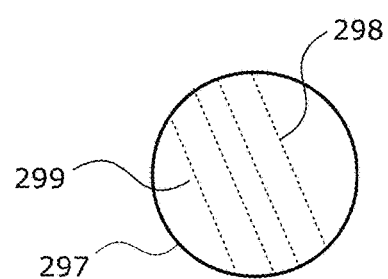
FIG. 24D
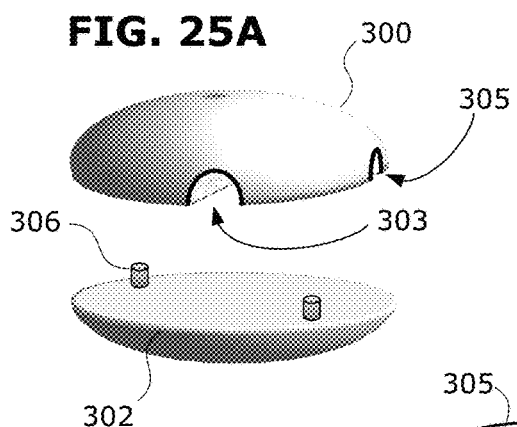
FIG. 25A
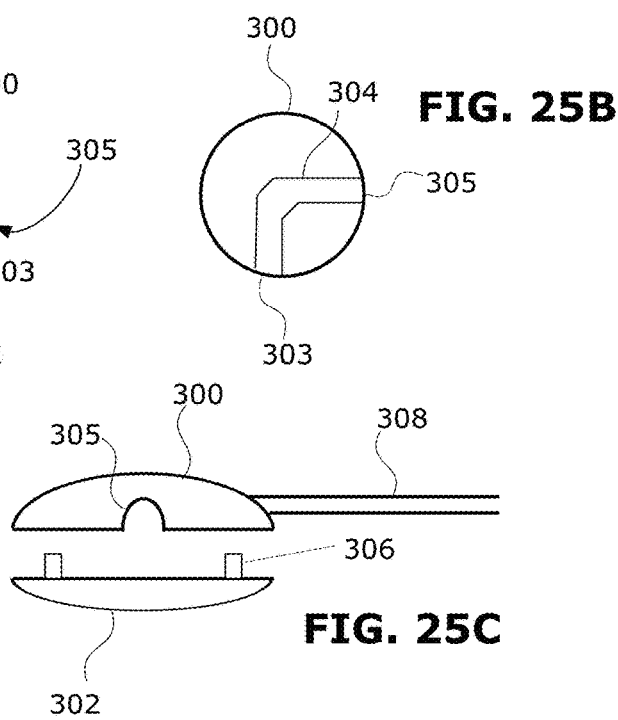
FIG. 25B
FIG. 25C

FIG. 29C
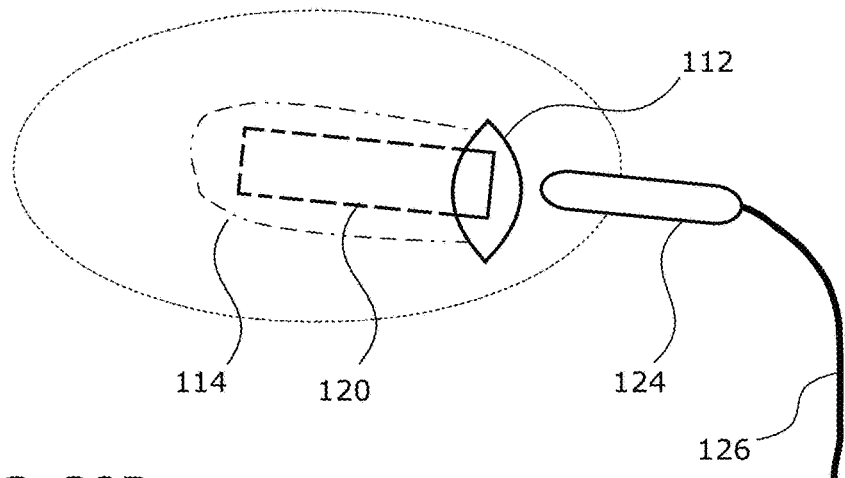
FIG. 29D
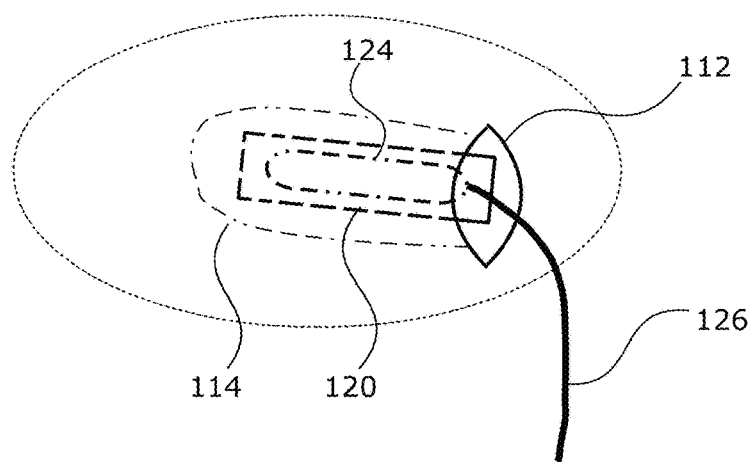
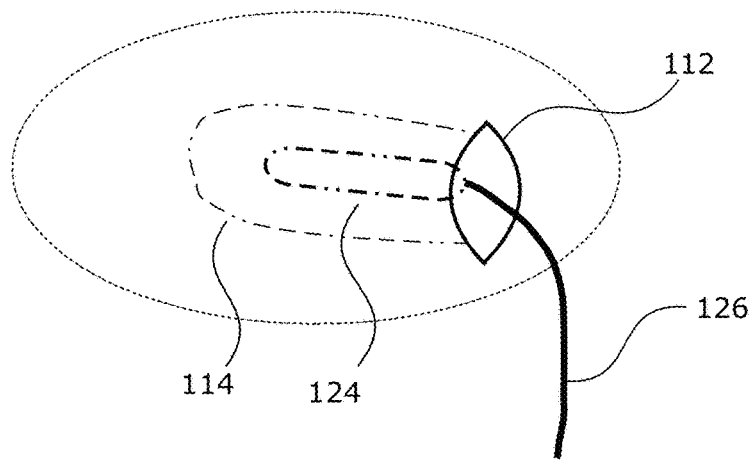
FIG. 29E

CRANIOFACIAL NEUROSTIMULATION FOR TREATMENT OF PAIN CONDITIONS

TECHNICAL FIELD

My invention relates to electrical neurostimulation for the treatment of pain conditions.

BACKGROUND

My invention relates to peripheral nerve neurostimulation (also known as electrical neuromodulation) for treatment of pain conditions. My invention is particularly useful for neurostimulation of the occipital nerves located at the back of the head/neck area. There are a number of problems with neurostimulation in this location (posterior region of the head/neck). Hypermobility in the head/neck area can cause lead migration resulting from traction on the lead caused by the twisting, turning, flexing, and bending of the head, neck, arms, or shoulders. This hypermobility can also cause increased stress on the lead, which can cause lead fracture or breakage. Conforming to the craniofacial anatomy can cause the lead wire to take sharp turns that further exacerbate the problem of fracture or breakage. My invention is directed to addressing these or other problems that occur in applying neurostimulation on the patient's head. The products and methods described herein can be used in other peripheral nerve stimulation situations as well.

Conventionally, a neurostimulation apparatus includes a lead wire coupled to an implantable neurostimulation power source (also called a pulse or signal generator, such as those used in spinal cord stimulation, deep brain stimulation, or peripheral nerve stimulation). The neurostimulation power source generates the electrical signals (e.g. pulses) according to programmable stimulation parameters or features. The neurostimulation lead has multiple electrodes, which may be on the lead wire or separately on a lead body. An example of a conventional neurostimulation apparatus is shown in FIG. 1. In this example, the neurostimulation lead is a paddle-type lead. A paddle body 10 is connected to an electrode lead wire 20. On paddle body 10 there are multiple electrodes 16. At the proximal end of electrode lead wire 20 there are multiple terminal contacts 18 for connecting with an extension lead wire 24 (the proximal and distal directions are indicated). The apparatus further comprises a power source 22 connected to the extension lead wire 24. At the distal end of extension lead wire 24 there is a boot 26 that couples with electrode lead wire 20 at terminal contacts 18.

SUMMARY

The products and methods of my invention described herein may be particularly useful for peripheral nerve neurostimulation in the craniofacial region of the patient's body (e.g. temporal region of the head, supraorbital region, or the posterior head/neck region, such as the occipital region of the head). Any of the peripheral nerves in the craniofacial region may be targeted, such as the occipital nerve (e.g. greater or lesser occipital nerve), supraorbital nerve, infraorbital nerve, and/or auriculotemporal nerve. Multiple different nerves may be targeted simultaneously. The neurostimulation lead may be placed in any suitable orientation relative to the targeted nerve, such as being placed along the course of the nerve(s) or perpendicular to the course of the nerve(s). The electrode array of the neurostimulation lead may be positioned over the targeted nerve(s), i.e. superficial to the targeted nerve. In some cases, the neurostimulation lead is implanted such that there is a layer of fascia tissue between the electrode array and the targeted nerve. The leads may be placed either unilaterally or bilaterally depending on the pain distribution.

My invention can use already-known techniques for implanting such neurostimulation leads on the head, such as those described in Leonardo Kapural et al, "Peripheral Nerve Stimulation for Occipital Neuralgia: Surgical Leads" in *Prog Neurol Surg,* 24:86-95 (2011); Richard Weiner, "Subcutaneous Occipital Region Stimulation for Intractable Headache Syndromes" in *Prog Neurol Surg,* 24:77-85 (2011); Damien Ellens et al, "Peripheral Neuromodulation for Migraine Headache" in *Prog Neurol Surg,* 24:109-117 (2011); Michael Gofeld, "Anchoring of Suboccipital Lead: Case Report and Technical Note" in *Pain Practice,* 4(4): 307-309 (2004); Giorgio Lambru et al, "Occipital nerve stimulation in primary headache syndromes" in *Ther Adv Neurol Disord.,* 5(1):57-67 (2012 January); Terrence L. Trentman et al, "Occipital Nerve Stimulation: Technical and Surgical Aspects of Implantation" in *Prog Neurol Surg.,* 24:96-108 (2011); and Angelo Franzini et al, "Occipital nerve stimulation (ONS). Surgical technique and prevention of late electrode migration" in *Acta Neurochir* (2009).

My invention also encompasses methods of treating a pain condition in a patient. The pain condition is one that is amenable to treatment by craniofacial neurostimulation; examples of such include headaches, neuralgias in the head region, and fibromyalgia. Examples of headaches that can be treated include migraine headaches, cluster headaches, tension headaches, hemicrania continua, post-traumatic headache, cervicogenic headache, SUNCT-type headaches (short-lasting, unilateral, neuralgiform headache attacks with conjunctival injection and tearing), and SUNA-type headaches (short-lasting, unilateral, neuralgiform headache attacks with cranial autonomic symptoms). Examples of neuralgias that can be treated include supraorbital neuralgia, occipital neuralgia, and trigeminal neuropathic pain. Examples of target sites in the craniofacial region include the temporal region of the head, supraorbital region, or the posterior head/neck region, such as the occipital region (which includes the area below the external occipital protuberance and the C2 innervation region on the scalp).

The method is performed by implanting the neurostimulation lead under the skin (e.g. adjacent the fascia) at the target site. In some cases, the neurostimulation lead is implanted under the skin but superficial to fascia. The method may also include other conventional techniques such as routing of the lead wires by subcutaneous tunneling, creating strain relief loops, creating subcutaneous pockets, and implanting a pulse generator (e.g. at the back or buttocks).

BRIEF DESCRIPTION OF THE DRAWINGS

FIG. 7A shows the paddle lead implanted in the occipital region. FIG. 7B shows a small vertical skin incision used to extract this implanted lead. FIG. 7C shows the paddle body exposed and the anchoring sutures. FIG. 7D shows the paddle body being extracted. FIG. 7E shows closing of the skin incision.

FIGS. 8A-B shows a paddle-type neurostimulation lead with an angled lead wire. FIG. 8A shows the paddle body connected to the angled lead wire. FIG. 8B shows the range of possible angles.

FIGS. 17A-B shows how neurostimulation could be reprogrammed to remedy lead migration. FIG. 17A shows the original position of the lead. FIG. 17B shows the lead after it has migrated downward.

FIG. 20A is a perspective view of the lead wire anchor. FIG. 20B is a top, see-through view of the lead wire anchor. FIG. 20C shows the projected surface area of the lead wire anchor.

FIG. 21A shows a see-through top view of the lead wire anchor. FIG. 21B shows an ordinary top view of the lead wire anchor. FIG. 21C shows a transverse cross-section view of the lead wire anchor.

FIG. 23A shows a top view of the lead wire anchor. FIG. 23B shows a transverse cross-section view of the lead wire.

FIGS. 24A-D shows various other possible designs for a low profile lead wire anchor. FIG. 24A shows a lead wire anchor with a passageway in an "L"-shaped configuration. FIG. 24B shows a lead wire anchor with a passageway in a "T"-shaped configuration. FIG. 24C shows a lead wire anchor having dual straight passageways. FIG. 24D shows a lead wire anchor having dual straight passageways.

FIGS. 25A-C shows a two-piece lead wire anchor. FIG. 25A shows a perspective view of the lead wire anchor. FIG. 25B shows a bottom view of the top piece of the lead wire anchor. FIG. 25C shows a side view of the lead wire anchor.

FIG. 28A shows a perspective view of the introducer tool. FIG. 28B shows a longitudinal cross-section, close-up view of the introducer tool.

FIGS. 29A-E shows a method for implanting a paddle lead in the occipital region of the head/neck using an introducer tool. FIG. 29A shows a vertical midline incision on the posterior head/neck. FIG. 29B shows the introducer tool inserted into a transversely oriented subcutaneous tunnel. FIG. 29C shows the paddle body being inserted into the hollow channel of the introducer tool. FIG. 29D shows the paddle body advanced through the introducer tool. FIG. 29E shows the paddle body in the subcutaneous tunnel after the introducer tool is withdrawn.

FIG. 30A shows a top view of the neurostimulation lead. FIG. 30B shows a transverse cross-section view of the ribbon lead wire.

FIG. 31A shows a top view of the neurostimulation lead. FIG. 31B shows the neurostimulation lead as implanted. FIG. 31C shows the neurostimulation lead with a bend in the ribbon lead wire.

FIG. 32A shows a top view of the neurostimulation lead. FIG. 32B shows the neurostimulation lead with the ribbon lead wire folded over.

DETAILED DESCRIPTION

A. Paddle Lead (1-8 Below)

One aspect of my invention is a paddle-type neurostimulation lead comprising a lead wire and a paddle body that is designed for use in the craniofacial region (e.g. the occipital region on the posterior head/neck). The paddle lead has dimensions suitable for implantation at the intended craniofacial site (e.g. the occipital space at posterior head/neck). The paddle body can have any suitable shape or geometry, and the array of electrodes on the paddle body can have any suitable configuration. The paddle body can be made of any flexible plastic or fabric material suitable for implantation in the body such as silicone, polyurethane, polyether ether ketone (PEEK), polyvinyl chloride (PVC), epoxy resin, etc. The paddle body has one or more of the features as described below.

1. Dimensions.

Figure 1:
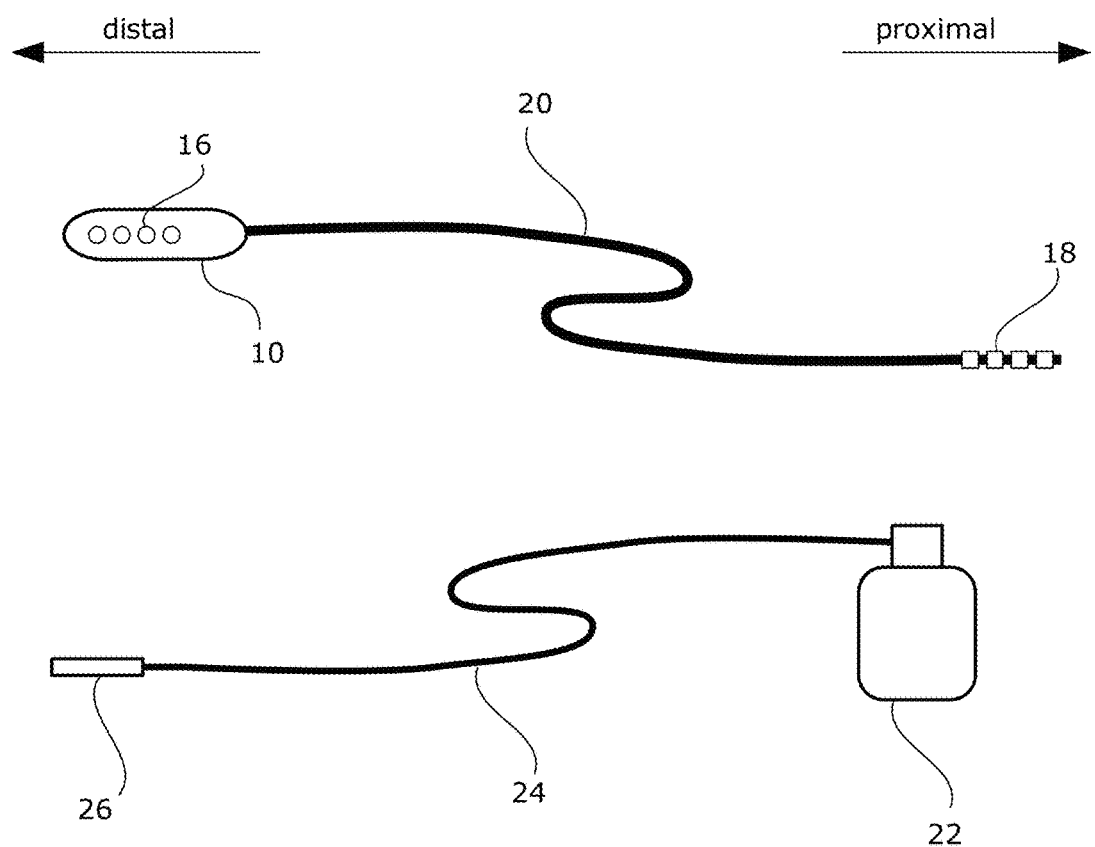
FIG. 1 shows an example of a conventional neurostimulation apparatus.
Figure 2:
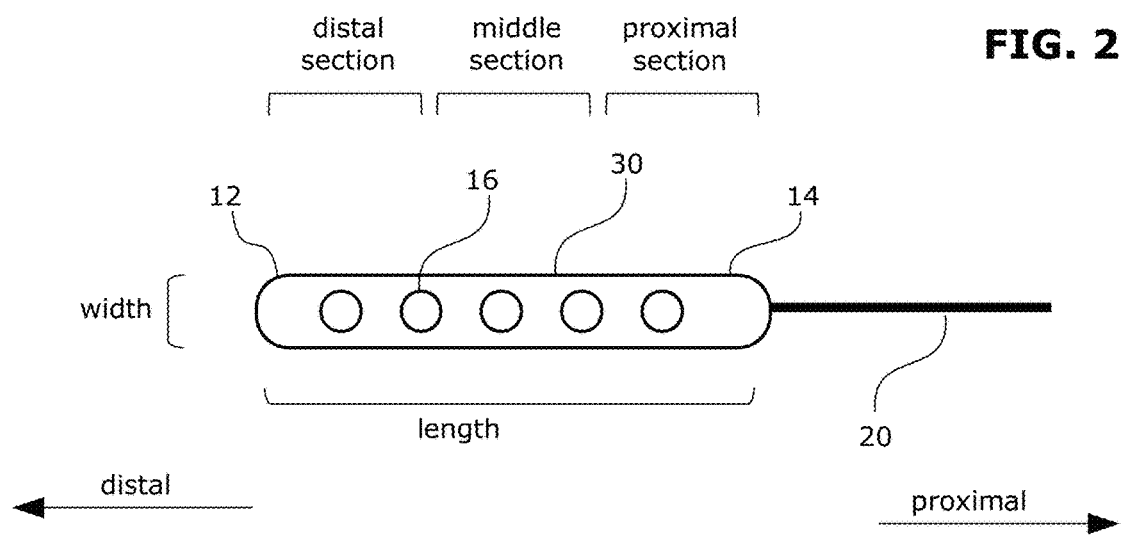
FIG. 2 depicts the width, length, and sections of a paddle body on a paddle-type lead.

The dimensions of the paddle body may be designed for particular use in the craniofacial region (e.g. the occipital region of the head). FIG. 2 depicts the width and length of a paddle body 30 of a paddle-type lead. As shown here, the paddle body 30 can be divided into three sections. There is a distal section 12, which is the distal one-third section of the paddle body 30; a proximal section 14, which is the proximal one-third section; and a middle one-third section in between.

The paddle body may be relatively wide. Making the paddle body wider may be beneficial in several ways. For example, it may allow more surface area for improved bio-adhesion or bio-encapsulation of the paddle body to reduce the incidence of lead migration. It could also reduce the incidence of hardware failures, improve patient comfort, reduce the incidence of erosion through the skin, or provide other benefits in craniofacial neurostimulation. In some embodiments of my invention, the width of the paddle body is 11 mm or wider; and in some cases, 13 mm or wider; and in some cases, 15 mm or wider.

The paddle body may be relatively thin. Reducing the thickness of the paddle body can be beneficial in improving patient comfort. For example, in some cases, the thickness of the paddle body is 1.6 mm or thinner; and in some cases, 1.3 mm or thinner. Making the paddle body longer may be beneficial in simplifying the surgical technique for implanting the paddle lead; for example, by ensuring that the target nerves are encompassed by the paddle body without requiring extensive manipulation or allowing the proximal end to be anchored to body tissue (e.g. underlying fascia) through the same incision in which the paddle body is inserted. In some cases, the length of the paddle body is 40 mm or longer; in some cases, 45 mm or longer; and in some cases, 50 mm or longer.

2. Curved Shape.

In some embodiments of my invention, the paddle body has a curved shape to conform to the craniofacial anatomy (e.g. at or near the occiput). Making the paddle body have a curved shape allows it to conform better with the body contours of the craniofacial anatomy, which can reduce the incidence of lead migration, reduce the incidence of hardware failure, improve patient comfort, or provide other possible benefits in craniofacial neurostimulation. The curvature is about a transverse axis (across the long axis) of the paddle body and with the electrodes being on the concave side of the curvature. In some embodiments, the paddle body is malleable (deformable by human manual manipulation) around a transverse axis and non-elastic such that it can be bent to form and retain a curved shape that conforms to the patient's body contour. In cases where such a malleable paddle body is used in methods of my invention, the method may further involve deforming the paddle body to conform to the patient's body contour at the target site of implantation.

Figure 3:
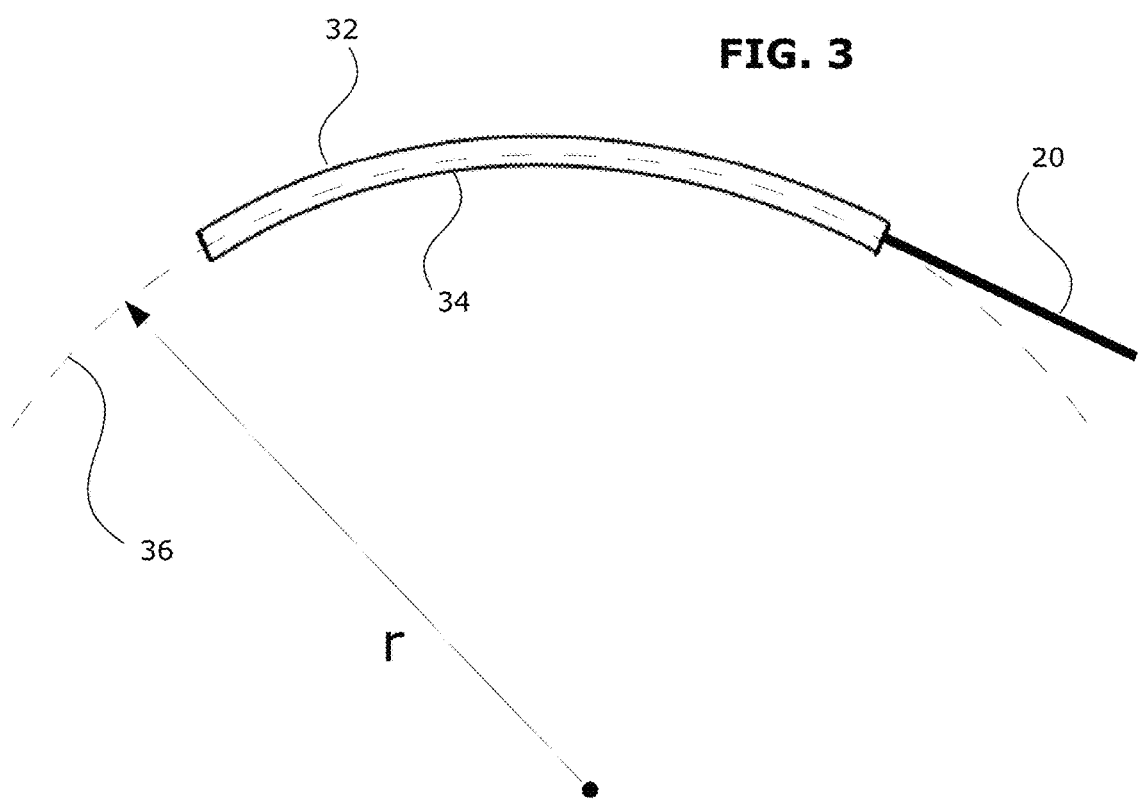
FIG. 3 shows a curved paddle body.

In some embodiments, the paddle body has a preset curvature designed for use "as is." The paddle body does not necessarily have to be rigid to maintain the preset curvature. It can be flexible, but still be sufficiently resilient that it will return to its natural curvature after the deforming force is released. To conform with the craniofacial anatomy (e.g. the posterior head/neck region), the radius of the preset curvature is in the range of 4-11 cm as determined by best-fit analysis. FIG. 3 shows an example of a best-fit radius of curvature applied to a curved paddle body 32. As seen in this side view, the paddle body 32 has a curved shape. The dotted line 36 shows the outline of the circle that best-fits the curvature of the paddle body 32. The radius (r) of the best-fitting circle 36 is the best-fit radius of curvature applied to the curved paddle body 32. The electrodes of the paddle body 32 are located on its concave side 34. The "best-fit" circle can be determined in any suitable manner. For example, it can be determined computationally by least squares analysis (for example, Microsoft Excel® has a feature for computing a best fit circle), graphical measurements by tracing an image of the paddle body, or estimated by visual inspection by drawing a circle that best fits the curvature of the paddle body.

3. Suture Holding Feature.

Figure 4A:
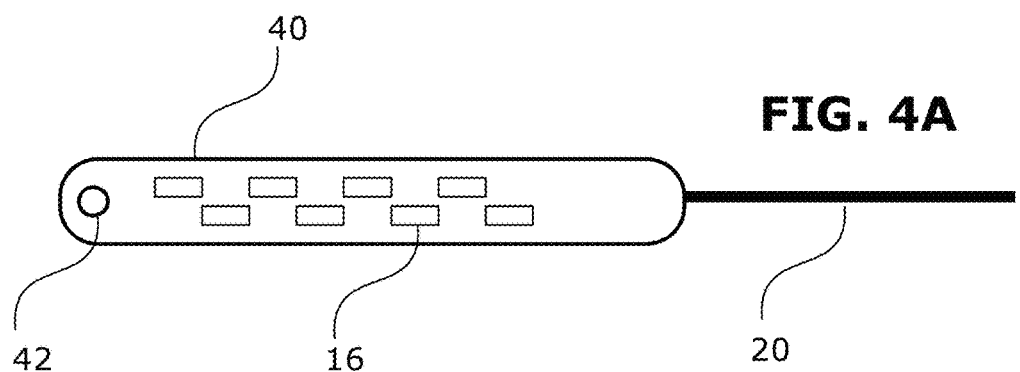
FIGS. 4A-D shows various configurations for a suture holding feature. In the example of FIG. 4A, the suture holding feature is a small hole for receiving a suture. In the example of FIG. 4B, the suture holding feature is an anchoring ring. In the example of FIG. 4C, the suture holding feature is a suture pad. In the example of FIG. 4D, the suture holding feature is a mesh.

There may be a suture holding feature attached to or built into the paddle body. As such, in some embodiments, the paddle body comprises a suture holding feature(s) to allow the paddle body to be secured onto body tissue (e.g. the underlying fascia). Examples of suture holding features include holes, apertures, eyelets, indentations, recesses, grooves, tags, tabs, collars, rings, wings, fingers, knobs, bumps, hooks, posts, ridges, ribs, threading, tines, barbs, pins, or other such structures that can hold a suture. In some embodiments, the suture holding features is placed at the distal end, proximal end, and/or lateral side of the paddle body. In some embodiments, a suture holding feature is located on the distal end of the paddle body. In the example shown in FIG. 4A, there is a small hole 46 at the distal tip of paddle body 40 for receiving a suture.

Figure 4B:
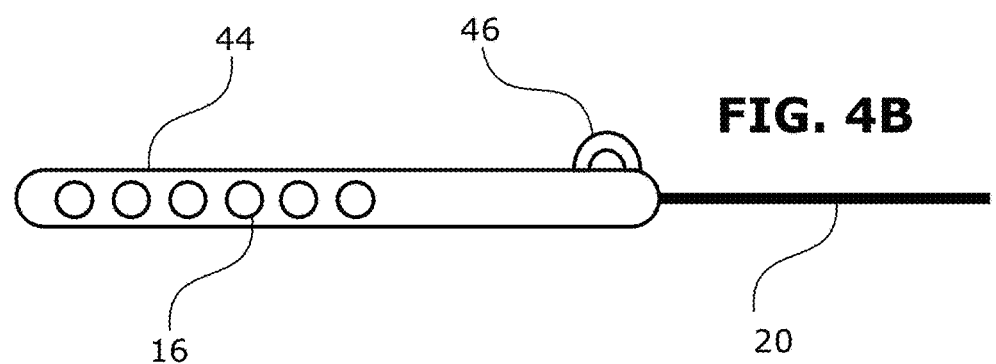

In some embodiments, the paddle body has a suture holding feature located somewhere on the proximal one-third section of the paddle body (see definition above). There may be further suture holding feature(s) somewhere on the distal one-third section of the paddle body. In some embodiments, there is a suture holding feature located somewhere on the proximal one-third section of the paddle body, but not on its distal one-third section. For example, as shown in FIG. 4B, there is an anchoring ring 46 on the proximal one-third section of the paddle body 44, but no such anchoring ring on its distal section.

In some embodiments, a suture holding feature is located on a lateral side of the paddle body. An example of this is shown in FIG. 4B, in which the anchoring ring 46 is located on the lateral side of the paddle body 44 near the proximal end (in this case, the cephalad/superior side of the paddle body 44, as oriented when implanted on the left side of the patient's body).

For those having a laterally-located suture holding feature, paddle bodies intended for implanting on the left side of the patient may have a different configuration from those intended for implanting on the right side of the patient, and vice versa. In such cases, in some embodiments, the suture holding feature is located on the cephalad side (i.e. superior side) of the paddle body (as oriented when implanted on the left or right side of the patient).

Figure 4C:
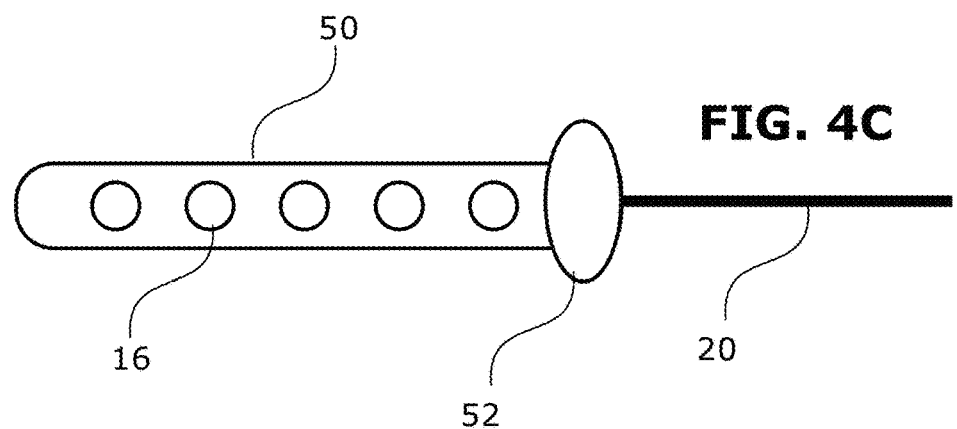
Figure 4D:
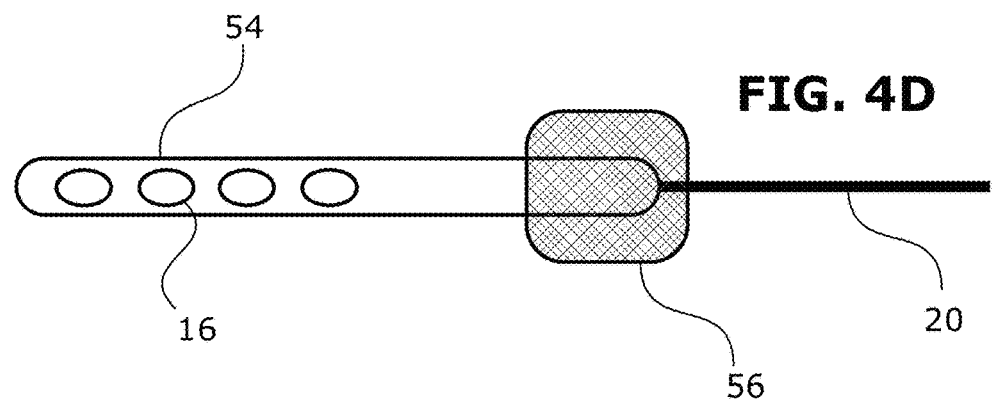

Other examples of suture holding features are shown in FIGS. 4C and 4D. In FIG. 4C, at the proximal end of paddle body 50, there is a pad 52 to be anchored by sutures. In FIG. 4D, the proximal end of paddle body 54 is anchored by a mesh 56 that is secured to body tissue by sutures.

Figure 5:
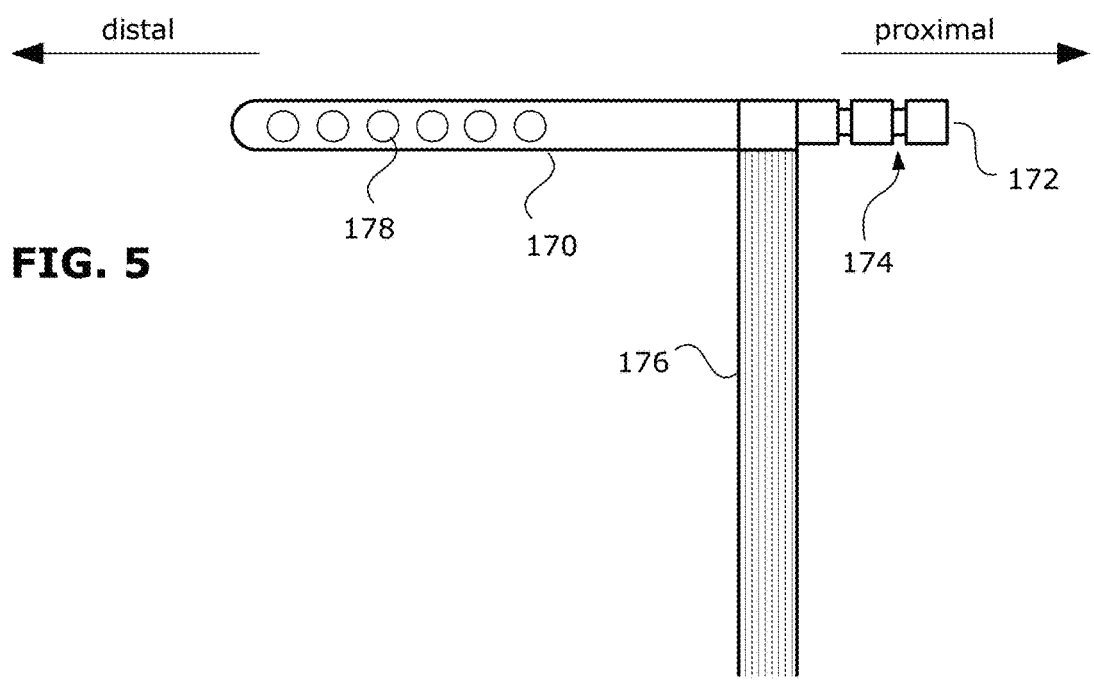
FIG. 5 shows a paddle body having a grooved post for holding sutures.
Figure 6:
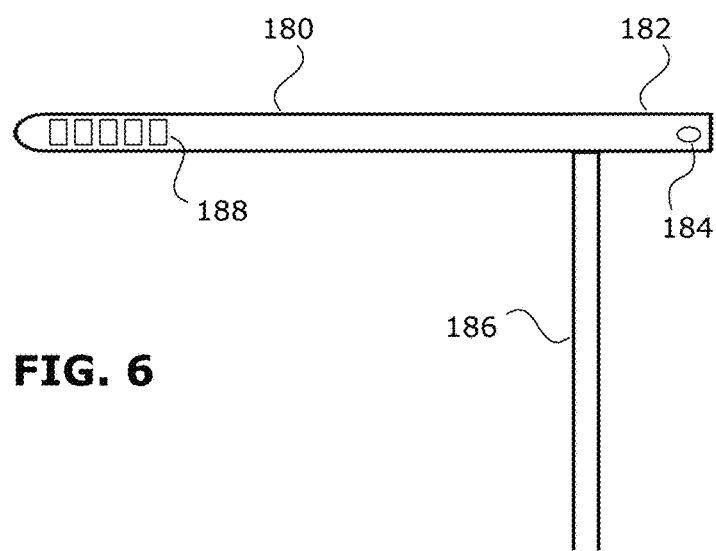
FIG. 6 shows a paddle body with a proximal extension that has a suture eyelet for holding a suture.

FIG. 5 shows another example. Here, there is a post 172 at the proximal end of the paddle body 170. The post 172 has grooves 174 to hold sutures. The paddle body 170 has multiple electrodes 178, which are connected via a ribbon lead wire 176 (as further explained in section E below). As seen here, the ribbon lead wire 176 is connected to paddle body 170 at an angle (as further explained below). FIG. 6 shows another example. Here, the paddle body 180 has a proximal extension 182. The proximal extension 182 has a suture eyelet 184 for inserting a suture. The paddle body 180 has multiple electrodes 188, which are connected via a conventional cylindrical lead wire 186. As seen here, the cylindrical lead wire 186 is connected to paddle body 180 at an angle (as further explained below).

4. Proximal Section Anchoring.

In another aspect, my invention is a method of implanting a paddle-type lead (having a paddle body) with anchoring somewhere at the proximal one-third section but not the distal end of the paddle body. By implanting a paddle lead in this manner, the paddle body can be anchored through the same incision through which the paddle body is subcutaneously introduced. As such, there is no need for making a separate incision on the skin overlying the distal end of the paddle body to anchor it.

Having a paddle lead implanted in this manner also allows for easier extraction of the lead if lead extraction is subsequently needed (e.g. because of infection or device failure). Having the paddle body anchored at the proximal section but not the distal end can allow for extraction of the paddle body without having to make a separate skin incision at the distal end of the paddle body.

Figure 7A:
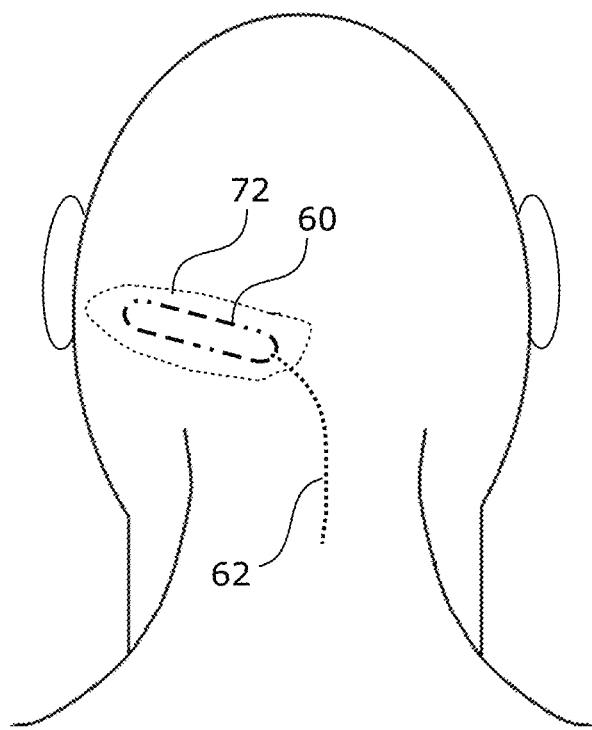
FIGS. 7A-E shows a method for performing a lead extraction.
Figure 7B:
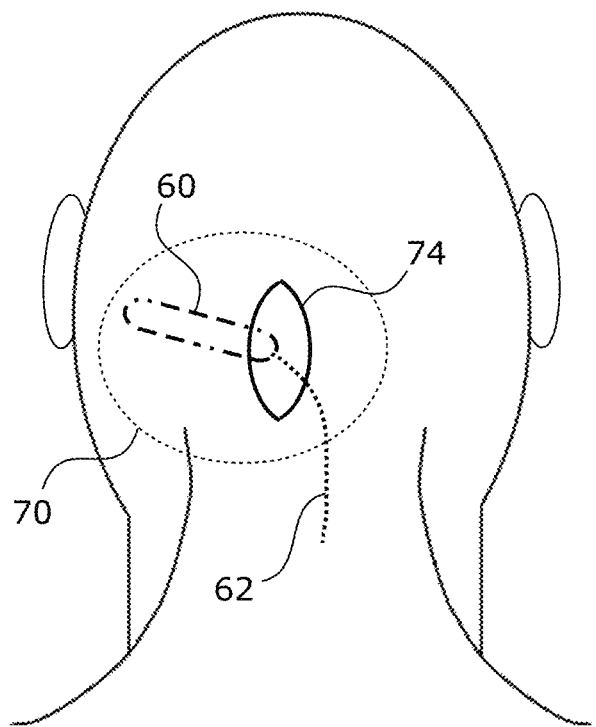
Figure 7C:
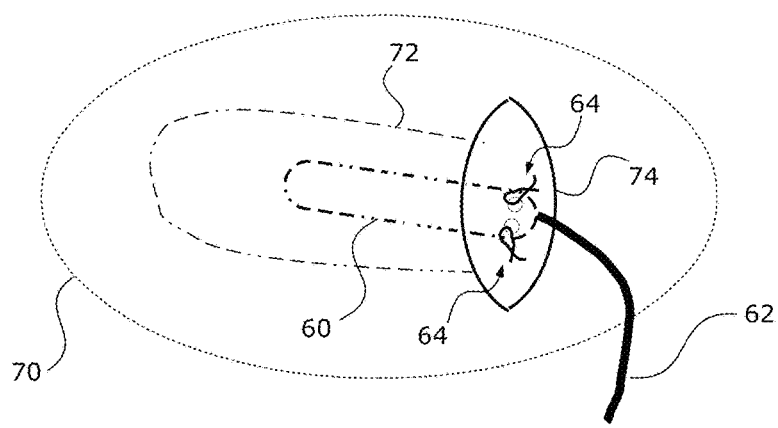
Figure 7D:
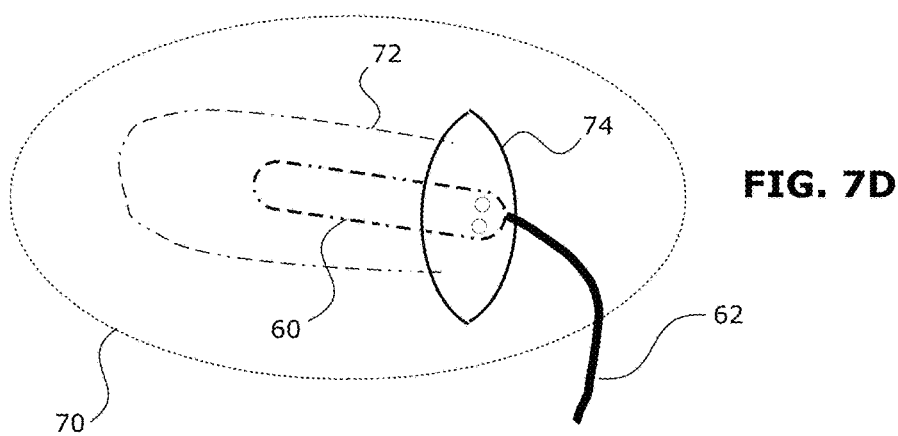
Figure 7E:
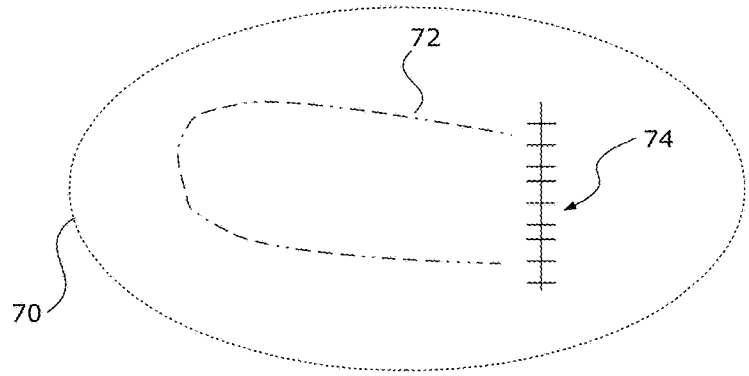

An example of how a lead extraction can be performed according to a method of my invention is shown in FIGS. 7A-E. As shown in FIG. 7A, the patient has a paddle lead (with paddle body 60 and lead wire 62) implanted in a subcutaneous tunnel 72 in the occipital region of her head. As shown in FIG. 7B, to extract this implanted lead, the clinician makes a small vertical skin incision 74 near the proximal end of the paddle body 60 (i.e. sufficiently close that the proximal end of the paddle body 60 is exposed by retraction of the skin tissue overlying it). The oval area 70 is shown in isolation in FIGS. 7C-E. FIG. 7C shows the proximal end of the paddle body 60 exposed and the sutures 64 that anchor the paddle body 60 (through the two small holes shown) to the underlying fascia. The clinician removes these anchoring sutures 64. As shown in FIG. 7D, the sutures 64 have been removed and the paddle body 60 is extracted. As shown in FIG. 7E, after the paddle body 60 is extracted, the skin incision 74 is sutured closed. Because in this scenario, the paddle body 60 did not have any anchoring at its distal end, the clinician was able to extract the paddle body 60 without having to make a separate incision at its distal end to unanchor it.

5. Angled Lead Wire.

Another aspect of my invention is a special alignment of the lead wire in relation to the paddle body. In conventional paddle leads, the lead wire extends out straight from the proximal end of the paddle body. However, for this embodiment of my invention, the lead wire extends out at an angle from the longitudinal axis of the paddle body along the plane of the paddle body. This feature could be useful for avoiding sharp turns in the lead wire that can promote damage to the lead wire. This could also be useful for orienting the direction of the paddle body laterally while allowing the lead wire to travel in a more caudal direction.

In some embodiments, the angle between the paddle body (along its longitudinal axis) and the lead wire extending out of the paddle body is in the range of about 90° to 150° along the plane of the paddle body. This angle is measured with vector for the paddle body longitudinal axis pointing in the distal direction and the vector for the lead wire pointing away from the longitudinal axis. In a conventional paddle-type neurostimulation lead, the lead wire extends out the proximal tip of the paddle body at 180° angle on the longitudinal axis.

In some cases, the angle is in the range of 100° to 140°; and in some cases, the angle is in the range of 110° to 150°. As shown in the example of FIG. 8A, the paddle body 80 is connected to lead wire 82 via a connector 86. The lead wire 82 extends out from the proximal end of the paddle body 80 at an angle instead of extending straight out. As shown in FIG. 8B, the angle 88 in which the lead wire 82 extends out from the paddle body 80 can range from about 90° to 150° relative to the longitudinal axis of the paddle body 80.

The lead wire does not necessarily have to connect to the paddle body at its proximal end. In some embodiments, the lead wire connects to the paddle body not at the proximal end of the paddle body, but instead somewhere at a point between the distal end and the proximal end of the paddle body. In some cases, the lead wire connects to the paddle body at a middle one-third section or proximal one-third section of the paddle body. In some cases, the lead wire connects to a lateral side of the paddle body (e.g. inferior/caudal side). Having the lead wire connected in this manner can help balance the traction on the paddle body resulting from the lead wire being pulled downward.

Figure 9:
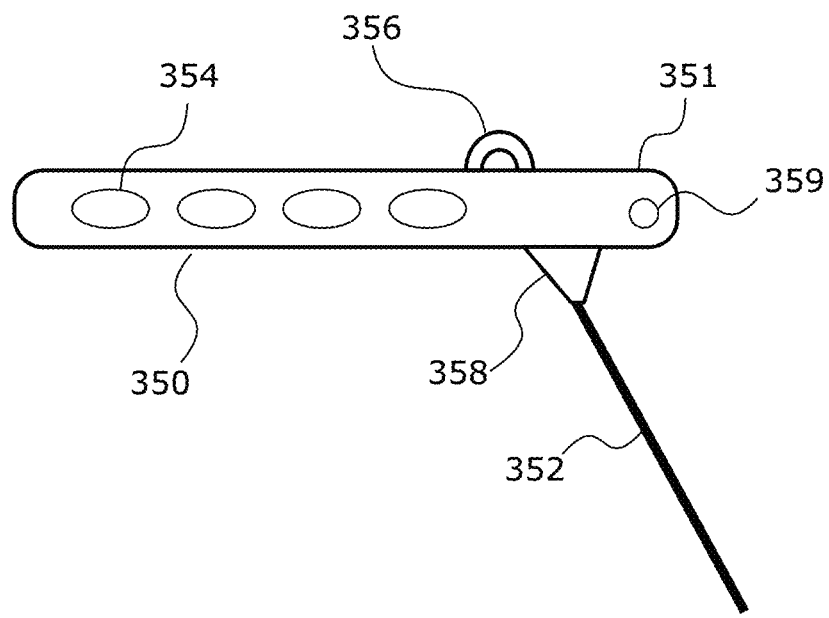
FIG. 9 shows another paddle-type neurostimulation lead with an angled lead wire.

FIG. 9 shows another example of a paddle-type neurostimulation lead with an angled lead wire. The neurostimulation lead comprises a paddle body 350 having electrodes 354 thereon. The paddle body 350 is connected to lead wire 352 via a connector 358. The lead wire 352 extends out from the lateral, inferior/caudal side of the paddle body 350 at an angle. The paddle body 350 also has an anchoring ring 356 on the lateral, superior/cephalad side of the paddle body 350. The paddle body 350 also has a proximally-extending portion 351 that has a suture opening 359. The paddle body 350 is anchored by passing a suture through anchoring ring 356 and another suture through suture opening 359. This example also demonstrates an embodiment of my invention in which the paddle body comprises a suture holding feature at a location somewhere proximal to where the lead wire connects to the paddle body.

Figure 10:
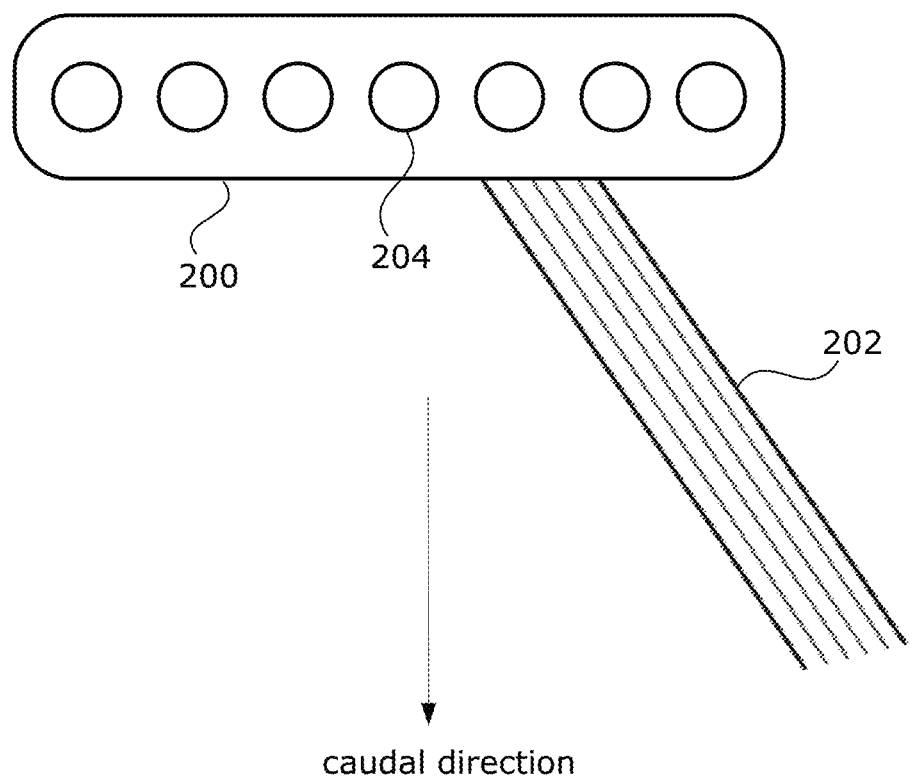
FIG. 10 shows a paddle-type neurostimulation lead with an angled ribbon lead wire.

The lead wire can be a ribbon lead wire as described in section E below. As shown in the example of FIG. 10, a ribbon lead wire 202 is connected to a paddle body 200 which has multiple electrodes 204. The ribbon lead wire 202 is connected to the paddle body 200 on its inferior lateral side at a point between the ends of the paddle body 200. The ribbon lead wire 202 extends out from the paddle body 200 at an angle relative to the longitudinal axis of the paddle body 200. This angle points the lead wire in a caudal direction on the patient.

6. Bilateral Paddle Lead.

Some patients require occipital neurostimulation on both sides of the head (bilateral neurostimulation). To address this situation, another embodiment of my invention is a neurostimulation lead comprising a bilateral paddle body that extends to both sides of the midline. This paddle lead could be used for simultaneous bilateral neurostimulation. The paddle body may be sufficiently long to cover the greater occipital nerve on both sides of the patient's head/neck. In some embodiments, the length of the bilateral paddle body is at least 9 cm long; in some cases, at least 12 cm long; in some cases, at least 15 cm long.

There are multiple electrodes on the paddle body. In some embodiments, the paddle body comprises a left-side wing and a right-side wing. There is a first set of electrodes on the left wing of the paddle body and a second set of electrodes on the right wing of the paddle body. In some embodiments, the distance between the medial-most electrode (i.e. towards the middle) on the left wing and the medial-most electrode on the right side is at least 3 cm wide. In some embodiments, the outer-most electrode of the first set of electrodes (left side) is within 1 cm of the tip of the left wing and the outer-most electrode of the second set of electrodes (right side) is within 1 cm of the tip of the right wing.

The left and right wings are not necessarily defined by the electrode configuration on the paddle body. The left and right wings may be defined by the lead wire connecting to the paddle body at a location somewhere between the distal and proximal ends of the paddle body. In some embodiments, the lead wire connects to the paddle body somewhere at a middle one-third section (see definition above) of the paddle body. In some embodiments, the lead wire connects to the paddle body at a point within 3 cm distance of the midline of the paddle body (between the proximal and distal ends of the paddle body).

Figure 11:
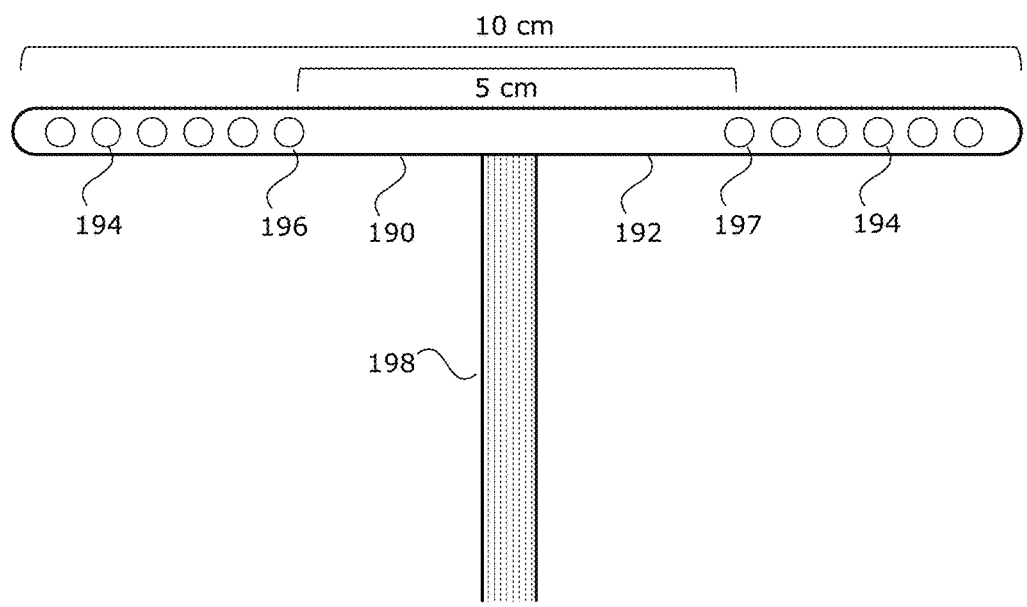
FIG. 11 shows a bilateral paddle-type lead.

FIG. 11 shows an example of a bilateral paddle-type lead. The paddle body comprises a left wing 190 and a right wing 192. The paddle body spans a length of 10 cm. There are multiple electrodes 194 on the paddle body that are connected via a ribbon lead wire 198 (as further explained in section E below). There is a first set of electrodes 194 on the left wing 190 and a second set of electrodes 194 on the right wing 192. The distance between the medial-most electrode 196 on the left wing and the medial-most electrode 197 on the right wing is 5 cm.

Figure 12:
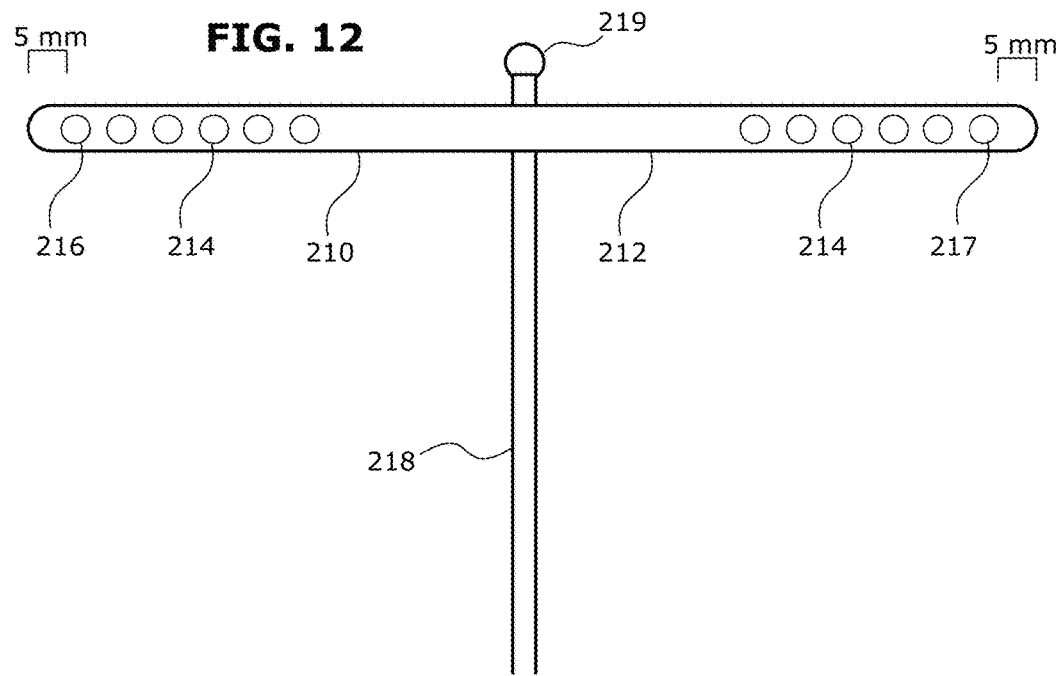
FIG. 12 shows another bilateral paddle lead with a suture knob.

The configuration of a bilateral paddle lead may facilitate the placement of a suture holding feature (see above). In some embodiments, the paddle body further comprises a suture holding feature that is located somewhere between the distal and proximal ends of the paddle body (e.g. within 3 cm of the midline). FIG. 12 shows another example of a bilateral paddle lead. The paddle body comprises a left wing 210 and a right wing 212. There are multiple electrodes 214 on the paddle body that are connected via a conventional cylindrical lead wire 218. Outermost electrode 216 located on the left wing 210 is 0.5 cm from the left-most tip of the paddle body. Outermost electrode 217 located on the left wing 212 is 0.5 cm from the right-most tip of the paddle body. This paddle lead also has a suture knob 219 (to hold a suture) located in the middle of the paddle body, on the lateral superior side of the paddle body.

Figure 13:
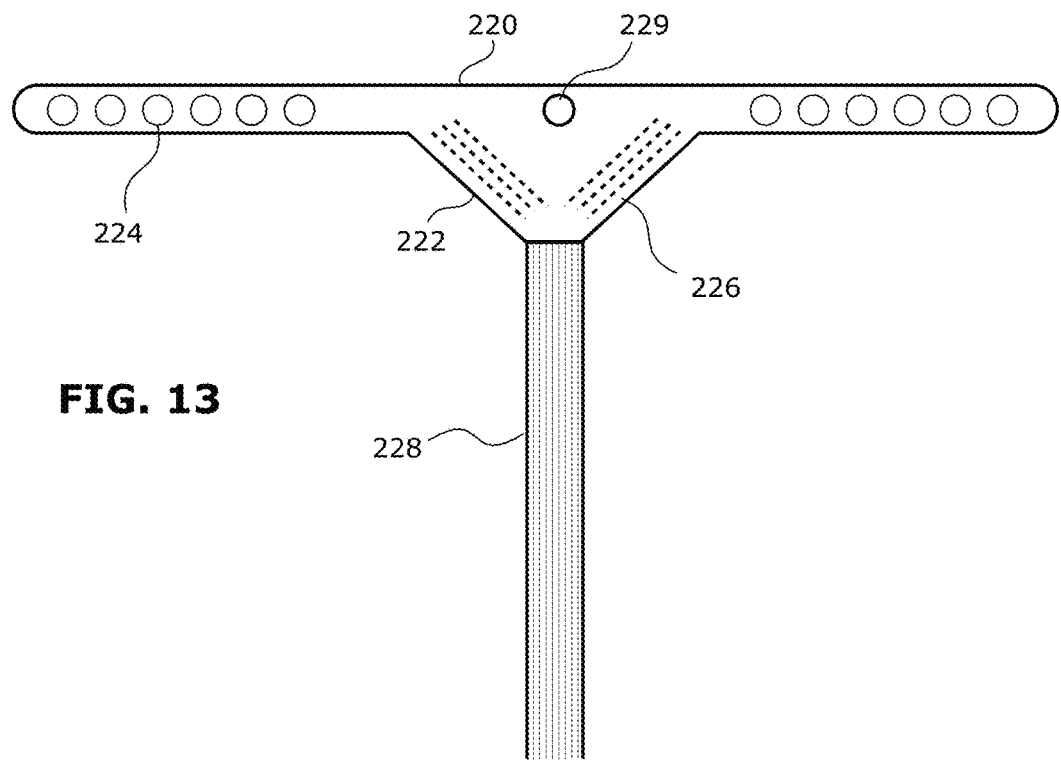
FIG. 13 shows a bilateral paddle lead with a suture opening.
Figure 14:
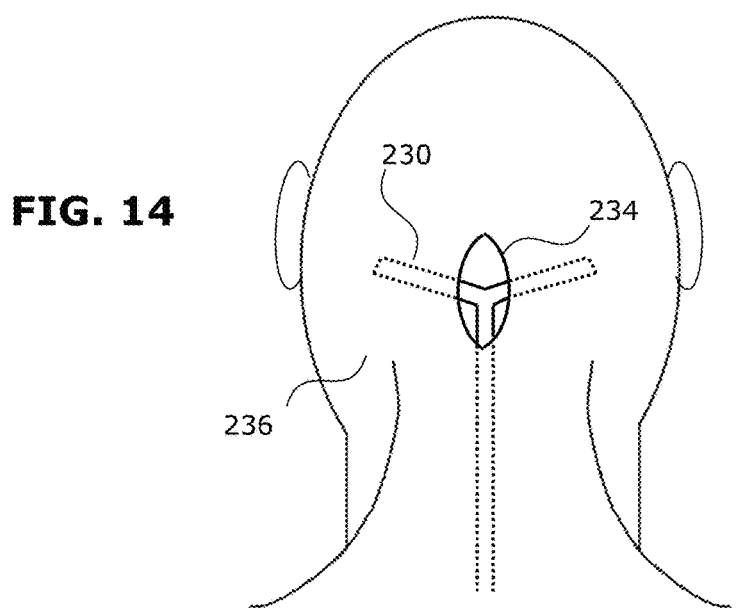
FIG. 14 shows a bilateral paddle lead as implanted.

FIG. 13 shows another example of a bilateral paddle lead. The paddle body 220 has multiple electrodes 224 thereon that are connected via a ribbon lead wire 228. The ribbon lead wire 228 connects to the paddle body 220 near its middle. The paddle body 220 has a suture opening 229 to allow suture insertion. The paddle body 220 also has a shoulder 222 to allow the conductive electrode wires 226 to pass around the suture opening 229 on its way to the ribbon lead wire 228. FIG. 14 shows an example of a bilateral paddle lead 230 as implanted through an incision 234 in a patient's posterior head/neck 236. Note that this particular bilateral paddle lead 230 has a V-shape instead of a linear shape.

7. Enlarged Distal End.

Another problem with occipital neurostimulation is lead erosion through the skin. Many people have little soft tissue cushioning at their back of the head/neck. Because of this lack of cushioning, hardware implanted in this region can erode through the skin. To address this problem, another embodiment of my invention is a neurostimulation lead comprising a paddle body with a relatively wider distal end.

In some embodiments, the paddle body has an enlarged distal end designed such that the surface area of the distal one-third section (see above definitions of proximal, middle, and distal one-third sections) of the paddle body is greater than the surface area of the proximal one-third section of the paddle body. In some cases, the distal one-third section of the paddle body has a surface area that is at least 30% greater than the surface area of the proximal one-third section of the paddle body.

In some embodiments, the width at the widest point in the distal one-third section of the paddle body is greater than the width at the widest point in the proximal one-third section of the paddle body; in some cases, the width at the widest point in the distal one-third section of the paddle body is at least 30% wider. In some cases, the width at the widest point in the distal one-third section of the paddle body is at least 8 mm wide; and in some cases, at least 12 mm wide.

The shape of this distal enlarged end of the paddle body may have fewer sharp corners that could promote skin erosion. In some embodiments, the enlarged distal end of the paddle body has a rounded shape (e.g. circular, ellipse-like, etc.). In some embodiments, the enlarged distal end of the paddle body has rounded corners (instead of sharp corners).

The distal enlarged end of the paddle body may be softer, thinner, or more flexible than the proximal one-third section of the paddle body. The distal enlarged end of the paddle body may be made of a different material than the proximal one-third section of the paddle body. The distal enlarged end of the paddle body may be made of a softer, thinner, or more flexible material (e.g. a softer polyurethane) than the proximal one-third section of the paddle body.

Figure 15:
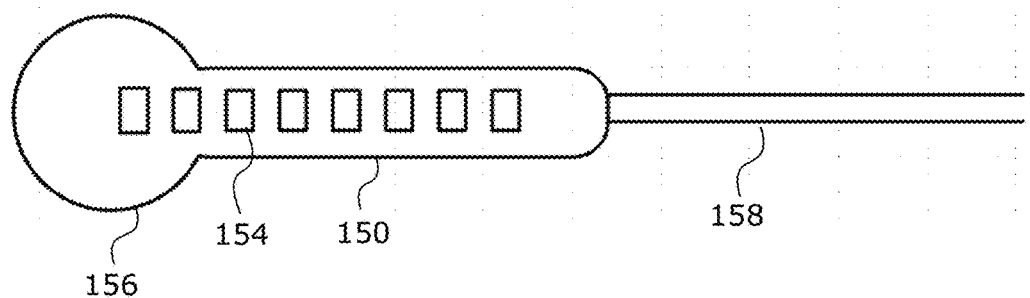
FIG. 15 shows a paddle-type neurostimulation lead with an enlarged distal end on the paddle body.

An example of a neurostimulation lead of my invention is shown in FIG. 15. The neurostimulation lead comprises a paddle body 150 having multiple electrodes 154 thereon. At its proximal end, the paddle body 150 is connected to a conventional cylindrical lead wire 158. The paddle body 150 has an enlarged distal end 156 with a circular shape.

Figure 16:
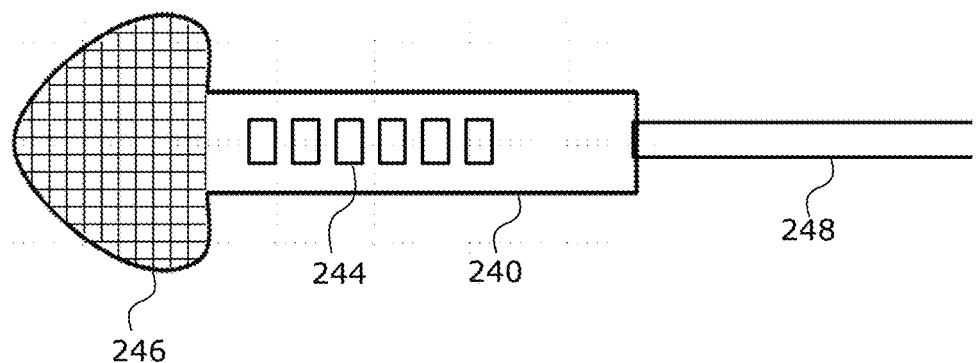
FIG. 16 shows another paddle-type neurostimulation lead with an enlarged distal end on the paddle body.

In some embodiments, the enlarged distal end of the paddle body is made in the form of a mesh. The mesh can be made of a plastic or a fabric material. Using a mesh can be beneficial for its flexibility or softness. In some embodiments, the mesh is porous. This can be advantageous for allowing tissue ingrowth or promoting tissue encapsulation, thereby improving fixation of the paddle body to body tissue. An example of a neurostimulation lead of my invention is shown in FIG. 16. The neurostimulation lead comprises a paddle body 240 having multiple electrodes 244 thereon. At its proximal end, the paddle body 240 is connected to a conventional cylindrical lead wire 248. The paddle body 240 has an enlarged distal end 246 that is made of a mesh material which is a different material than the more proximal portion of the paddle body 240.

8. Summary.

In one embodiment, my invention can be described as a paddle-type neurostimulation lead that comprises a paddle body having the dimensions as described above. In another embodiment, my invention can be described as a paddle-type neurostimulation lead that comprises a curved shaped paddle body as described above. In yet another embodiment, my invention can be described as a paddle-type neurostimulation lead that comprises a paddle body with a suture holding feature as described above. In yet another embodiment, my invention can be described as a paddle-type neurostimulation lead that comprises a paddle body with an angled lead wire as described above. In yet another embodiment, my invention can be described as a paddle-type neurostimulation lead that comprises a bilateral paddle body as described above. In yet another embodiment, my invention can be described as a paddle-type neurostimulation lead that comprises a paddle body with an enlarged distal end as described above. The paddle lead of my invention can have combinations of the features described above (e.g. the curved shape in combination with the suture holding feature). My invention also encompasses neurostimulator kits or sets that include such paddle leads (e.g. as a component in a neurostimulator apparatus kit), as well as including other components such as a power source (e.g. implantable pulse generator).

In another embodiment, my invention is a method of treating a pain condition in a patient by implanting a paddle-type neurostimulation lead of my invention into the patient's body. The paddle body is implanted under the skin at a craniofacial site on the patient's body (e.g. occipital region of the head). In some embodiments, the paddle body is implanted in an orientation across a greater occipital nerve (as opposed to alongside, running parallel to the nerve). In relevant embodiments of the neurostimulation lead, the method may comprise deforming the paddle body to conform to the patient's body contour at the target site of implantation.

In relevant embodiments of the neurostimulation lead, the method may comprise anchoring the paddle body to subcutaneous body tissue (e.g. fascia) by suturing the suture holding feature. In relevant embodiments of the neurostimulation lead, the paddle body may be inserted with the lead wire angled towards a caudal direction on the patient; in some cases, the lead wire is made to travel caudally down the patient's neck. In relevant embodiments of the neurostimulation lead, the left wing of the bilateral paddle body may be inserted on the patient's left side and the right wing of the bilateral paddle body may be inserted on the patient's right side; in some cases, the left wing of the paddle body is positioned over the left greater occipital nerve and the right wing of the paddle body is positioned over the right greater occipital nerve.

In relevant embodiments of the neurostimulation lead, the paddle body may be implanted with the enlarged distal end pointing towards the lateral side of the patient (as opposed to the patient's midline). In relevant embodiments of the neurostimulation lead, the method may comprise suturing the paddle body to body tissue at a proximal one-third section of the paddle body, but not on a distal one-third section. In relevant embodiments of the neurostimulation lead, the method may comprise suturing the paddle body at a lateral side of the paddle body; in some cases, at the lateral superior/cephalad side of the paddle body.

In relevant embodiments of the neurostimulation lead, the method may comprise suturing the paddle body to body tissue at a point on the paddle body that is proximal to where the lead wire connects to the paddle body. In relevant embodiments of the neurostimulation lead, the method may comprise suturing the paddle body to body tissue at a lateral side of the paddle body and further suturing the paddle body to body tissue somewhere at the proximal one-third section of the paddle body.

In yet another embodiment, my invention can be described as a method of implanting a paddle-type neurostimulation lead (having a paddle body) in the craniofacial region with anchoring somewhere at the proximal one-third section but not the distal end of the paddle body. The method comprises making a skin incision (which may be substantially vertical in orientation) at a site on the craniofacial region of the patient's body; inserting the paddle body of the paddle-type neurostimulation lead subcutaneously through the incision; within the same incision site, anchoring a proximal section of the paddle body to the fascia, but not at its distal end. In some cases, the paddle body at a proximal one-third section is anchored at least on its cephalad side. In some cases, the lead implantation method is performed without making a second incision on the craniofacial region at a site lateral to the first incision site. However, there may be other incision sites needed for implanting other components of the neurostimulation apparatus (e.g. an incision located caudally for placing an extension lead wire or a pulse generator).

In yet another embodiment, my invention can be described as a method of extracting a paddle-type lead (having a paddle body) that has been implanted in the craniofacial region of the patient. The method comprises making a skin incision (which may be substantially vertical in orientation) near the proximal end of the paddle body. After exposing the proximal end of the paddle body, the proximal section of the paddle body is detached from the body tissue (e.g. by removing any anchoring sutures). The paddle body is then extracted. In this method, only the proximal one-third section of the paddle body needs to be detached. As such, lead extraction can be accomplished without needing to make a separate incision over the distal end of the paddle body. In some cases, the lead extraction method is performed without making a second incision on the craniofacial region at a site lateral to the first incision site. However, there may be other incision sites needed for extracting other components of the neurostimulation apparatus (e.g. an incision located caudally for extracting an extension lead wire or a pulse generator).

B. Selectable Electrodes (1 & 2 Below)

Another aspect of my invention is a neurostimulation apparatus in which the electrodes on the neurostimulation lead are individually selectable. In this aspect of my invention, the neurostimulation apparatus includes a programmable power source, lead wire, and lead body (which can be cylindrical or paddle-type), wherein the electrodes on the lead body are individually selectable and the power source is programmable to individually activate the electrodes. This electrode selection feature may be particularly useful when lead migration occurs, in which the previously selected set of activated electrodes may no longer be effective (e.g. the lead has shifted and the active electrodes are no longer overlying the target nerve). Thus, a neurostimulation apparatus having this feature may be beneficial for leads implanted in the craniofacial region, where lead migration is particularly problematic because of the hypermobility in that part of the body.

1. Neurostimulation Apparatus.

In one embodiment, my invention can be described as a neurostimulation apparatus that comprises: a programmable power source (e.g. implantable pulse generator); a lead body (which can be cylindrical or paddle-type) having multiple electrodes; a lead wire connected to the lead body; wherein the electrodes on the lead body are individually selectable for activation and the power source is programmable to individually select the electrodes for activation. In some embodiments, a greater range of electrode selection is possible by having 6 or more electrodes on the lead body that are individually selectable; in some cases, there may be 8 or more individually selectable electrodes on the lead body; and in some cases, there may be 10 or more individually selectable electrodes on the lead body.

2. Reprogramming after Lead Migration.

This electrode selection feature can be used in a method in which, after diagnosing lead migration, the power source is reprogrammed to activate a different set of electrodes for neurostimulation. Neurostimulation leads placed in the craniofacial region often migrate in a medial and/or downward direction because of lead pullback or downward tugging on the lead.

As such, in some embodiments, the power source of the neurostimulation apparatus is reprogrammed to selectively deactivate one or more previously activated electrode(s) and selectively activate one or more previously inactive electrode(s). Selective activation of new electrodes may be improve the neurostimulation's effectiveness. Selective deactivation of electrodes may be useful for conserving battery power and/or avoiding stimulation of surrounding muscle or other non-targeted nerves.

In some cases, because of the direction in which the neurostimulation leads implanted in the patient's head (e.g. posterior head/neck region) tend to migrate, among the newly activated electrode(s), at least one of them is located distal to the previously activated set of electrodes; and among the now deactivated electrode(s), at least one of them was the proximal-most of the set of previously active electrodes on the lead.

An example of how this method can be implemented is shown in FIGS. 17A-B. FIG. 17A shows the original position of the cylindrical lead 90 when it was initially implanted. The set 94 (shown in hatching) of electrodes 92 are activated because they overlie the target nerve 98. FIG. 17B shows the lead 90 after it has migrated downward. The stimulation lead 90 is less effective because the set 94 of activated electrodes 92 are longer directly overlying the target nerve 98. As such, the neurostimulation apparatus is reprogrammed to activate a new set 96 (shown in hatching) of electrodes 92 that are better suited for the target nerve 98. As seen here, this new set 96 of activated electrodes is the result of activating electrode 95 and deactivating electrode 93, wherein the newly activated electrode 95 is located distal to the previously activated set 94 of electrodes and deactivated electrode 93 was the proximal-most of the previously activated set 94 of electrodes.

Accordingly, in another embodiment, my invention can be described as a method of adjusting the neurostimulation applied to a patient for a neurostimulation lead that has migrated. The patient has an implanted neurostimulation lead having multiple electrodes and a set (one or more) of the electrodes are activated, i.e. the power source is programmed to selectively activate that set of electrodes to provide neurostimulation. This can be useful in the situation when the implanted neurostimulation lead has migrated, which can be diagnosed by any suitable method (e.g. by x-ray examination or patient reporting loss of efficacy). The method comprises programming the power source to: (a) selectively deactivate one or more previously activated electrode(s), and (b) selectively activate one or more previously inactive electrode(s).

This method may be particularly useful for neurostimulation leads that are implanted in the craniofacial region (e.g. posterior head/neck region), in which lead migration tends to occur in a downward and/or transverse direction. In such cases, a newly activated electrode (of a previously inactive electrode) may be one that is located distal to the previously activated set of electrodes, and a newly deactivated electrode may be one that was the proximal-most of the set of previously activate electrodes on the lead.

C. Lead Wire Anchor (1-3 Below)

To address the problem of lead migration, another aspect of my invention is a lead wire anchor for securing the lead wire to body tissue. In general, the lead wire anchor of my invention has one or more passageways through which the lead wire travels. The passageway can be shaped to accept any of the various types of neurostimulation lead wires, including conventional rounded or cylindrical lead wires, or the ribbon-type lead wires as described above. The passageway can be enclosed (such as a tunnel, conduit, lumen, or channel) or open (such as a groove or trench). The lead wire anchor can be made of any flexible plastic or fabric material suitable for implantation in the body such as silicone, polyurethane, polyether ether ketone (PEEK), polyvinyl chloride (PVC), epoxy resin, etc. The lead wire anchor can have any suitable degree of flexibility/rigidity.

1. Curved Lead Wire Anchor.

An embodiment of my invention is a lead wire anchor that is especially suitable for use when implanting neurostimulation leads in tight spaces or on complex body contours, such as the craniofacial anatomy (e.g. posterior head/neck region), where the lead wire may be forced to take sharp turns. In this embodiment, the lead wire anchor has a curved shape that helps to control the turn angles taken by the lead wire, in particular, without excessively sharp bends or kinks, which can cause the wires to break, fracture, or lose insulation. With the anchor being curved, the orientation of the passageway at one end (the first location) is at an angle relative to the orientation of the passageway at the other end (the second location). In some embodiments, the passageway at the first location is oriented at an angle of 90° to 150° relative to the orientation of the passageway at the second location. This angle is measured with the vector at the first location in the passageway pointing outward and the vector at the second location in the passageway pointing outward. In some cases, the angle is in the range of 100° to 140°; and in some cases, in the range of 110° to 150°.

Figure 18A:
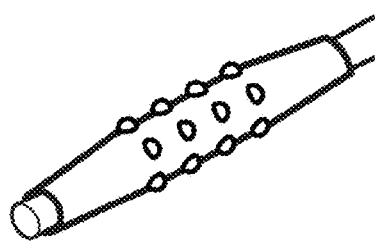
FIGS. 18A-B shows prior art lead wire anchors. In the example of FIG. 18A, the exits of the passageway are oriented at 180° relative to each other. Likewise, in the example of FIG. 18B, the exits of the passageway are oriented at 180° relative to each other.
Figure 18B:
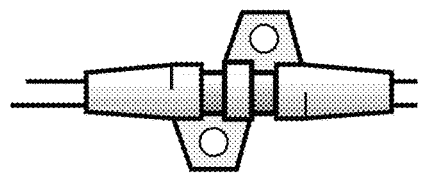
Figure 19:
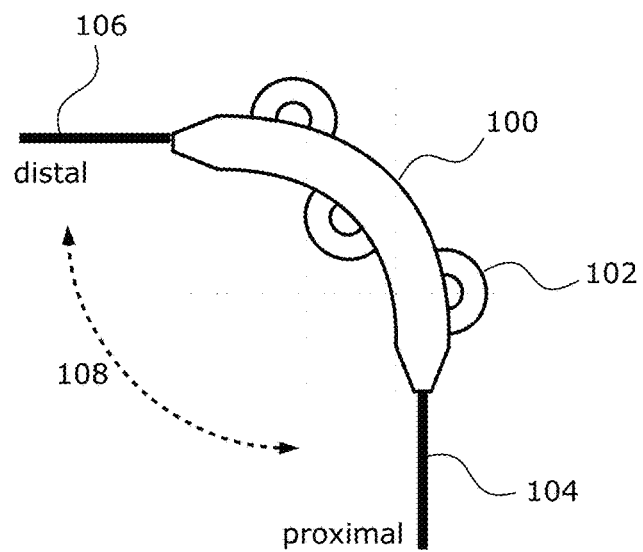
FIG. 19 shows a curved lead wire anchor.

FIGS. 18A and 18B show prior art lead wire anchors made by Medtronic. In these prior art lead wire anchors, the exits of the passageway are oriented at 180° relative to each other. FIG. 19 shows an example of a lead wire anchor 100 of my invention. The lead wire anchor 100 is made in a bended configuration such that the angle 108 between the lead wire 106 exiting from the distal end of the anchor and the lead wire 104 exiting the proximal end is in the range of about 90° to 150°; in some cases, in the range of 100° to 140°; and in some cases, in the range of 110° to 150°. The lead wire travels through a passageway in the lead wire anchor 100.

In another embodiment, my invention is a method of implanting a neurostimulation lead in the craniofacial region using such a curved lead wire anchor. The method comprises making a skin incision at a craniofacial site (e.g. posterior head/neck region); inserting a neurostimulation lead subcutaneously through the incision; within the same incision site, bending the lead wire at an angle in the range of about 90° to 150°; in some cases, at an angle in the range of 100° to 140°; and in some cases, at an angle in the range of 110° to 150° (with 180° being a straight line direction with no bending of the lead wire) as it transitions from a transversely-oriented direction to a caudally-oriented direction; inserting or fitting the lead wire into a curved lead wire anchor, wherein the curved lead wire anchor maintains the bend in the lead wire; within the same incision site, attaching the curved lead wire anchor to the fascia (e.g. by sutures, staples, etc.).

2. Low Profile Lead Wire Anchor.

Many people have little soft tissue cushioning at their back of the head/neck. Because of this lack of cushioning, hardware implanted in this region can be uncomfortably palpable to the patient. This can also cause muscle soreness, skin irritation, or skin erosion. Another embodiment of my invention is a low profile lead wire anchor that can address this type of problem. The low profile lead wire anchor has a maximum height of 8 mm or less; in some cases, 5 mm or less.

In some embodiments, the maximum height of the lead wire anchor is one-third its width or less; in some cases, one-fifth its width or less. The term "width" in this context means the shorter of the planar dimensions of the anchor (i.e. width vs. length). The low profile lead wire anchor comprises a top surface and a bottom surface opposite to the top surface. The bottom surface is the surface which faces towards the patient's body when implanted; the top surface faces away from the patient's body. However, in cases where the anchor is top/bottom symmetric, non-directional, or otherwise not configured to be used in any particular top/ bottom orientation, this top/bottom designation may be considered artificial, arbitrary, or interchangeable, being used only to separately point to the different surfaces of the lead wire anchor. The lead wire anchor has a passageway through which the lead wire travels. The passageway extends from a first location to a second location, wherein neither of the first nor second locations is on the bottom surface.

Figure 20A:
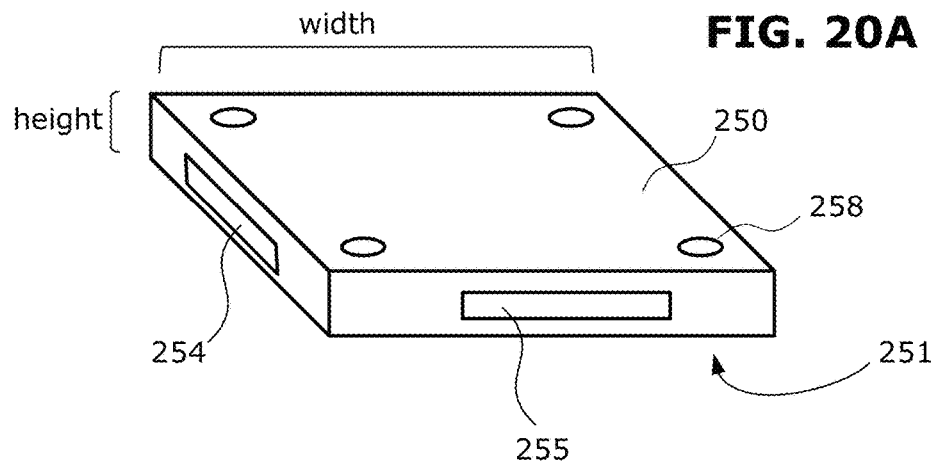
FIGS. 20A-C shows a low profile lead wire anchor.
Figure 20B:
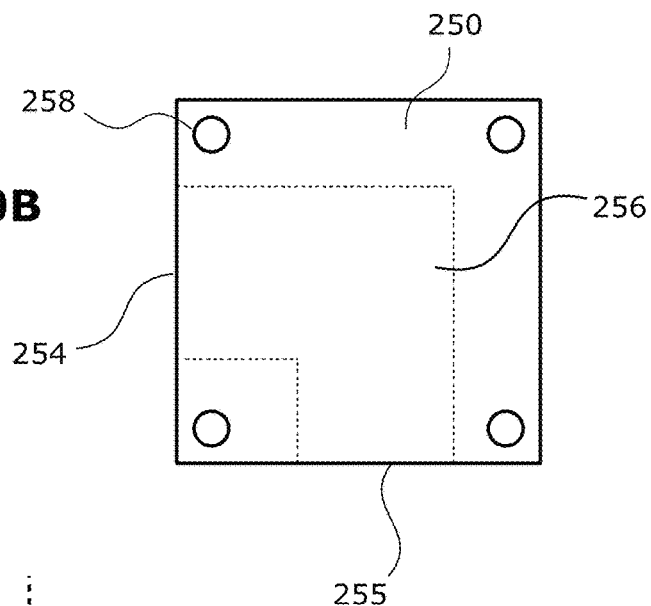
Figure 20C:
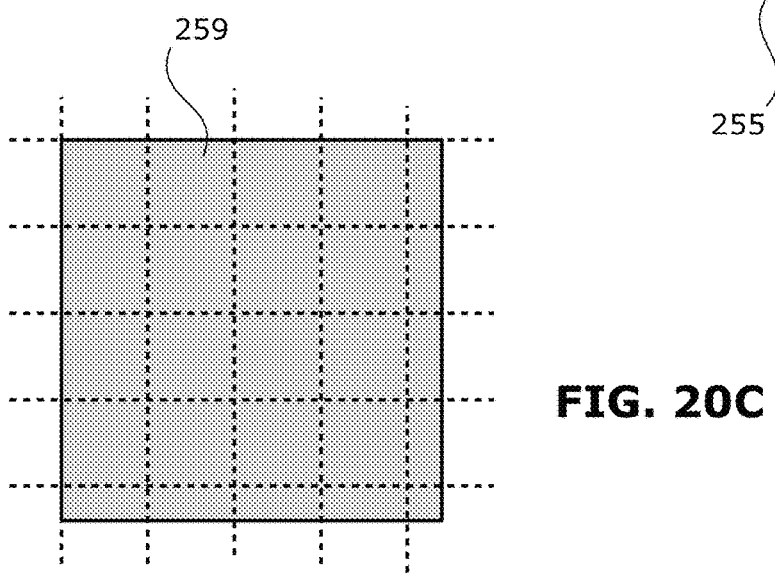

FIGS. 20A-C shows an example of a low profile lead wire anchor. As seen in FIG. 20A (perspective view), the lead wire anchor has a height that is substantially lower than its width. The lead wire anchor has a smooth top surface 250 and a smooth bottom surface 251. There is a passageway 256 traveling through the anchor to accommodate a ribbon-type lead wire. The passageway 256 extends from opening 254 to opening 255 on the adjacent side of the anchor. As shown in FIG. 20B (top see-through view), the passageway 256 has an "L" configuration. FIG. 20C shows the projected surface area of the lead wire anchor (as explained below).

2(a). Smooth Surface.

In some embodiments, the top surface is substantially smooth. A substantially smooth surface is beneficial because it distributes the pressure more evenly to reduce any pressure points that may cause discomfort for the patient. As used in this context, the term "smooth surface" means that, relative to the area of the surface, the lines defining the surface are discernably free (by unaided visual inspection) of any abrupt angles, abrupt bends, or abrupt surface changes, such as sharp projections, step-like elevations, prominences with square edges, deep indentations or recesses, or other uneven surface features.

Figure 21A:
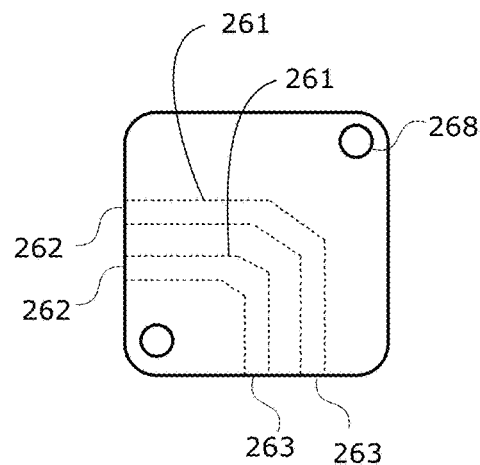
FIGS. 21A-C shows another low profile lead wire anchor.
Figure 21B:
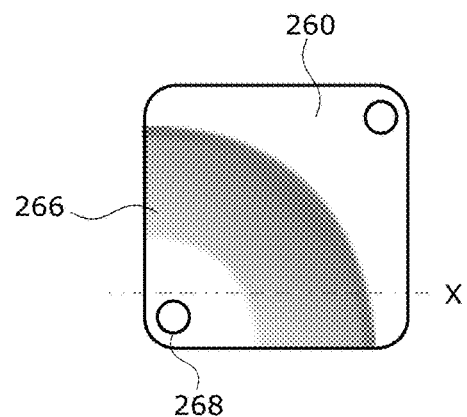
Figure 21C:
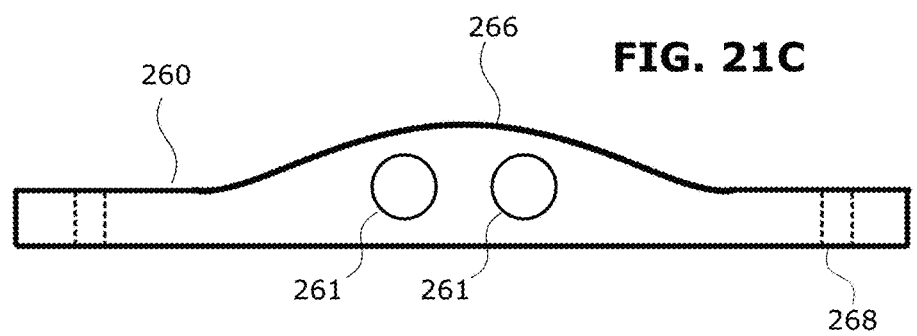

FIGS. 21A-C shows another example of a low profile lead wire anchor. As shown in FIGS. 21A (see-through top view) and 21B (ordinary top view), there are two parallel passageways 261 that travel through the anchor, each with an opening 262 located on one side of the anchor and an opening 263 located on an adjacent side of the anchor (and orthogonally oriented to each other). FIG. 21C is a transverse cross-section view through the dashed line "X" in FIG. 21B. As seen here, the top surface 260 of the anchor has a smooth bump 266 to accommodate the passage of the lead wires. The anchor also has two suture openings 268 for holding a suture.

2(b). Passageway.

The passageway can be shaped to accommodate the corresponding lead wire, whether it is a conventional cylindrical lead wire, a ribbon lead wire as described in section E below, or any other type of lead wire. In some embodiments, the height of the passageway is one-third its width or less. This may be useful for accepting a ribbon lead wire. In some cases, the height of the passageway is one-fifth its width or less.

In some embodiments, the passageway takes a non-straight path within the horizontal plane of the lead wire anchor. The horizontal plane is a plane parallel to the plane of the body tissue surface onto which the anchor is implanted. With this passageway configuration, the lead wire can follow a non-straight path within the lead wire anchor. This can be beneficial for redirecting the lead wire in a different direction (e.g. towards a caudal direction). Another possible benefit of this non-straight path is that it may increase frictional coupling between the lead wire and the anchor.

Figure 22:
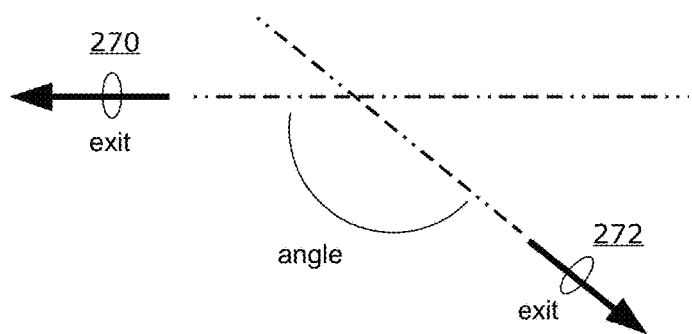
FIG. 22 shows the orientation vectors for determining the angle.

The passageway may be oriented to turn the path of the lead wire, i.e. making the lead wire switch directions. The orientation of the passageway at one end (at the first location) may be at an angle relative to the orientation of the passageway at the other end (at the second location). In some embodiments, the passageway at the first location is oriented at an angle of 90° to 150° relative to the orientation of the passageway at the second location. This angle is measured with the vector at the first location in the passageway pointing outward and the vector at the second location in the passageway pointing outward. In some cases, the angle is in the range of 100° to 140°; and in some cases, in the range of 110° to 150°. For example, FIG. 22 shows the orientation vector 270 at one end (exit) of a passageway and the orientation vector 272 at the other end of the passageway. Shown here is the angle between the two orientation vectors. A lead wire traveling through this passageway would change direction in this manner.

2(c). Shape.

The low profile lead wire anchor is generally flat and may have a relatively large surface area. This may be useful because it allows for a larger contact surface that distributes any pressure over a wider area, which can lessen discomfort for the patient. In some embodiments, the anchor has a projected surface area of at least 4.0 cm$^2$; and in some cases, at least 6.5 cm$^2$.

In this context, "projected surface area" means that, if the anchor were to be laid flat on a horizontal surface, the projected area is a two-dimensional area measurement of the anchor by rectilinear parallel projection onto the horizontal plane below the anchor. This can be performed in any suitable way, including mathematical modeling of the object or empirically by taking a direct overhead photograph of the object and making scaled measurements of the two-dimensional image in the photograph.

Figure 23A:
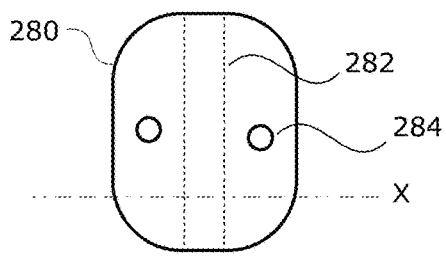
FIGS. 23A-B shows a lead wire anchor having convex-shaped surfaces.
Figure 23B:
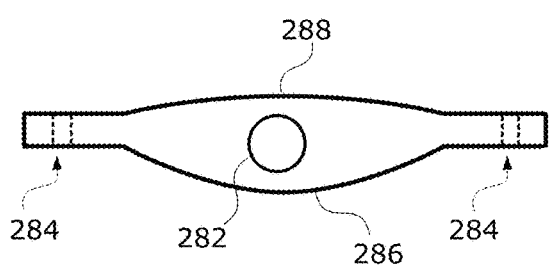

In some embodiments, the bottom surface of the anchor has a convex shape. When implanting the anchor at the back of the neck, this could be beneficial for conforming to the vertically-oriented nuchal furrow at the back of the neck (between the muscular columns on both sides of the midline). In some cases, the shape of the top surface is different from the shape of the bottom surface (asymmetric). For example, the shape of the top surface may be less convex (i.e. flatter) than the shape of the bottom surface. FIGS. 23A-B shows an example of a lead wire anchor of my invention. The lead wire anchor 280 has a convex bottom surface 286. As shown in FIG. 23A (top view), there is an internal passageway 282 traveling through the lead wire anchor 280. There are also two suture openings 284 to hold sutures that secure the lead wire anchor 280 to body tissue. FIG. 23B shows a transverse cross-section view of the lead wire anchor 280 taken along the dashed line "X" in FIG. 23A. This view shows the smooth top surface 288 of the lead wire anchor 280 and the bottom surface 288. As seen here, both the top surface 288 and the bottom surface 286 have a convex shape. However, the top surface 288 is less convex (flatter) than the bottom surface 286.

FIGS. 24A-D shows various other possible designs for a low profile lead wire anchor. FIG. 24A shows a lead wire anchor 290 having a single passageway 291 in an "L"-shaped configuration. FIG. 24B shows a lead wire anchor 292 having a passageway 293 in a "T"-shaped configuration. FIG. 24C shows a lead wire anchor 294 having dual straight passageways 295 and 296. FIG. 24D shows a lead wire anchor 297 having dual straight passageways 298 and 299.

3. Summary.

The lead wire anchor of my invention may also comprise a suture holding feature so that it can be secured onto the underlying body tissue (e.g. fascia). The lead wire anchor may be engaged with the lead wire in any suitable way, including being slidable within the anchor or being tightly fastened to the anchor (e.g. by using a locking mechanism or gripping surface). The lead wire anchor can be a single standalone unit or it may be provided in multiple (two or more) components that are designed to be fitted together. For example, the lead wire anchor may have two half-portions that the surgeon snaps or twists-on together to form the lead wire anchor of my invention.

As an example, FIGS. 25A-C shows a two-piece lead wire anchor. As shown in FIG. 25A (perspective view), the lead wire anchor has a top piece 300 (giving its substantially smooth top surface) and a bottom piece 302 (giving its bottom surface) that snap together via mating posts 306. As shown in FIG. 25B (bottom view of the top piece 300), there is an "L"-shaped open groove 304 at the bottom of the top piece 300 for accommodating a cylindrical lead wire. The groove 304 extends from opening 303 to opening 305. As shown in FIG. 25C (side view), both the top piece 300 and the bottom piece 302 have a smooth convex surface. FIG. 25C also shows a cylindrical lead wire 308 coupled to the top piece 300.

My invention encompasses a kit comprising a lead wire anchor as described above in combination with a neurostimulation lead (including those described herein as well as any other suitable type of neurostimulation lead). The lead wire anchor in this kit is configured to engage with the lead wire of the neurostimulation lead.

In another embodiment, my invention is a method of implanting a neurostimulation lead into a patient, wherein the neurostimulation lead comprises a lead wire. The method further comprises anchoring the lead wire (e.g. at a site on the back of the patient's head/neck) with a lead wire anchor of my invention as described above. The lead wire is made to bend in the anchor. In some embodiments, the lead wire is engaged with the passageway of the lead wire anchor such that the orientation of the lead wire in the passageway at the first location is at an angle relative to the orientation of the lead wire in the passageway at the second location. In some embodiments, the method further comprises suturing the lead wire anchor to subcutaneous body tissue (e.g. cervical fascia); in some cases, the lead wire anchor is implanted at a position below the patient's external occipital protuberance; in some cases, the lead wire anchor is implanted at the back of the patient neck. In some embodiments, the lead wire anchor is implanted on the nuchal furrow at the back of the patient's neck.

D. Introducer Tool (1-6 Below)

Figure 26:
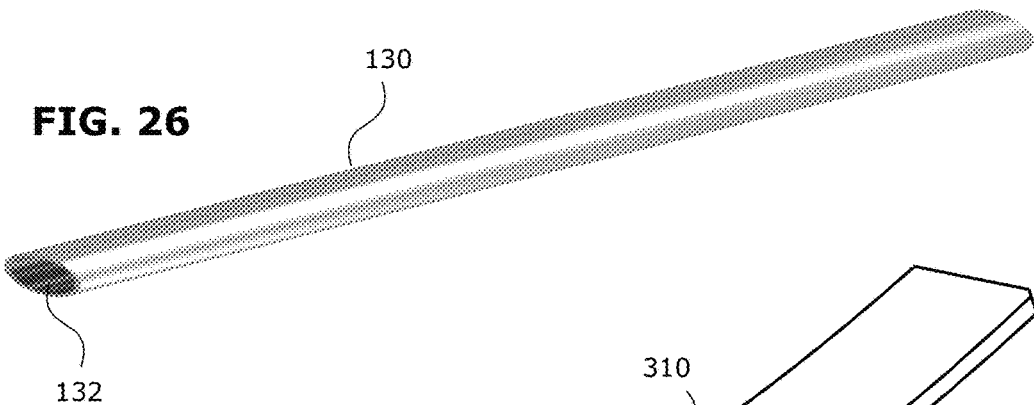
FIG. 26 shows an introducer tool.

In another aspect, my invention is an introducer tool used for inserting a paddle lead into a subcutaneous tunnel made in the craniofacial region (e.g. posterior head/neck region). As an example, FIG. 26 shows a perspective view of an introducer tool 130 of my invention. There is a hollow channel 132 through introducer tool 130.

1. Dimensions and Shape.

The introducer tool is shaped and has dimensions suitable for conforming with the craniofacial anatomy (e.g. posterior head/neck region). The introducer tool is hollow and has a generally elongate shape, and in transverse cross-section, the introducer tool has a non-circular shape. Examples of non-circular shapes include oval and generally rectangular shapes. As seen in FIG. 26, the height of the introducer tool (the dimension when laid flat on a surface) is less than its width.

The introducer tool may be used to help steer the paddle body to the optimal position for effective neurostimulation. As such, to prevent excess play of the paddle body inside the hollow channel of the introducer tool, the introducer tool may be made with dimensions that fit tightly around the thickness and/or width of the paddle body. In some embodiments, the hollow channel of the introducer tool has width and/or height dimensions that provide a clearance of less than 2 mm around the maximum width and/or maximum thickness of the paddle body for which the introducer tool is paired with (e.g. in a neurostimulator kit or set, such as a neurostimulator apparatus kit or neurostimulator implantation tool set); in some cases, the clearance is less than 1.5 mm around the maximum width and/or maximum thickness of the paddle body. In some embodiments, the height of the hollow channel of the introducer tool is in the range of 1.1-1.9 mm. In some embodiments, the width of the hollow channel of the introducer tool is in the range of 6.0 mm to 21.0 mm wide. In some embodiments, the width of the hollow channel of the introducer tool is 8.0 mm or wider; in some cases, 10.0 mm or wider; in some cases, 12.0 mm or wider. To facilitate insertion of the paddle body into the introducer tool, the hollow channel of the introducer tool may have a friction-reducing coating, such as polytetrafluoroethylene (PTFE).

2. Curved Shape.

In some embodiments of my invention, the introducer tool has a curved shape to conform to the craniofacial anatomy (e.g. at or near the occiput). The curvature is about a transverse axis (across the long axis) of the introducer tool. In some embodiments, the introducer tool is malleable (deformable by human manual manipulation) around a transverse axis and non-elastic such that it can be bent to form and retain a curved shape that conforms to the patient's body contour. In cases where such a malleable introducer tool is used in methods of my invention, the method may further involve deforming the introducer tool to conform to the patient's body contour.

Figure 27:
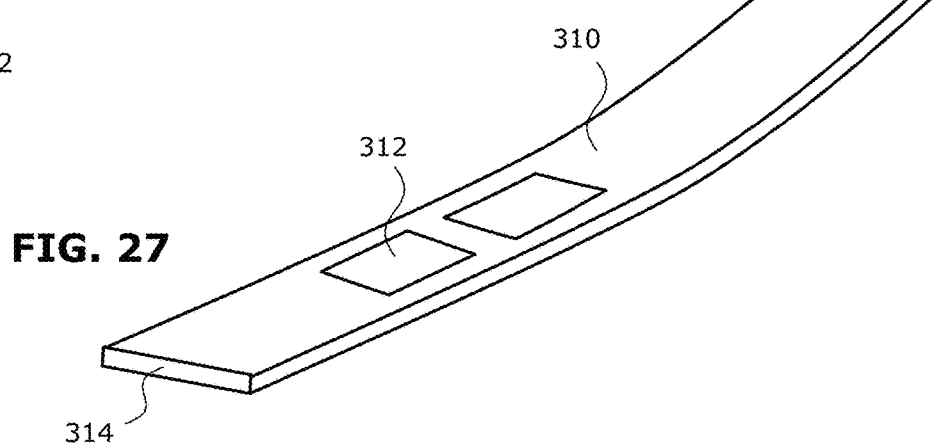
FIG. 27 shows a curved introducer tool with cut-out windows.

In some embodiments, the introducer tool has a preset curvature. The introducer tool does not necessarily have to be rigid to maintain the preset curvature. It can be flexible, but still be sufficiently resilient that it will return to its natural curvature after the deforming force is released. To conform with the craniofacial anatomy (e.g. the posterior head/neck region), the radius of the preset curvature is in the range of 4-11 cm as determined by best-fit analysis (see above description). FIG. 27 shows an example of a curved introducer tool. The tool has curved shape with a concave surface 310. On this concave surface 310, there are two cut-out windows 312 to allow for transmission of the electric field (see explanation below). The tool also has a hollow channel 314 to accommodate a paddle-type lead.

3. Non-Sharp Edge.

In some embodiments, the distal end of the introducer tool has a non-sharp edge (e.g. blunt, dull, rounded, etc., as opposed to a sharp edge such as straight or cutting edges). Having a non-sharp edge can be useful for helping to prevent damage to the paddle lead (e.g. to the electrical insulation) during manipulation while it is being implanted.

Figure 28A:
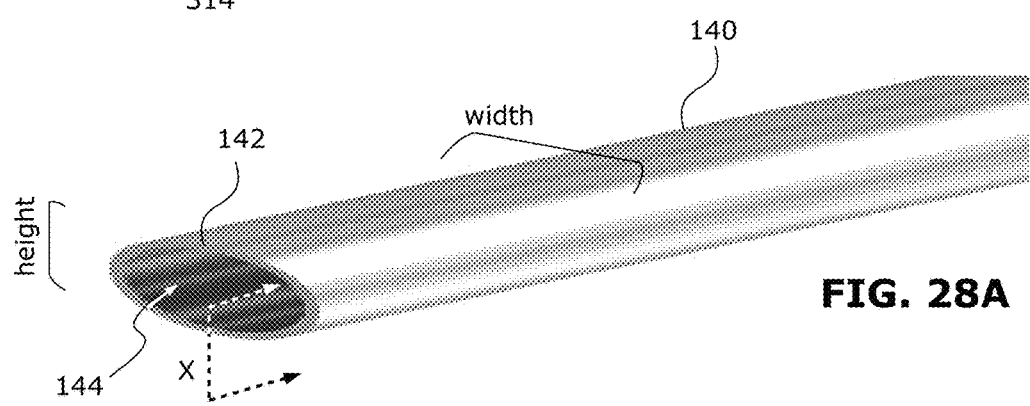
FIGS. 28A-B shows an introducer tool with a non-sharp edge.
Figure 28B:
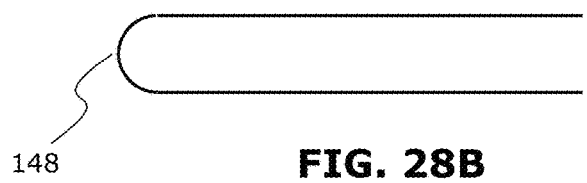

For example, FIG. 28A shows a distal end 142 of an introducer tool 140 according to one such embodiment. The introducer tool 140 has a hollow channel 144. FIG. 28B (longitudinal cross-section) shows a close-up view of the distal edge of the introducer tool 140 as seen on a cross-section taken at the dashed line "X" in FIG. 28A. As seen here, the distal end of the introducer tool 140 has a rounded edge 148 instead of a sharp edge. This can help to prevent the edge 148 from cutting into the neurostimulation lead as it is being manipulated while inside the introducer tool. Because it has this rounded edge 148, introducer tool 140 may not be effective for sharp cutting through tissue. As such, it is not intended to be used in such a manner. However, it is possible that it can be used for blunt dissection instead of cutting dissection.

4. Electric Field Permeability.

Because the introducer tool may be used to help steer the paddle body to the optimal position for effective neurostimulation, in some embodiments, the introducer tool is designed to allow the electric field stimulation to occur while the paddle body is inside the introducer tool, i.e. the emitted electric field can penetrate through the wall of the introducer tool. The introducer tool can be designed in a variety of different ways to accommodate this.

In some cases, the introducer tool has slots, cut-out windows, or other type of aperture to allow for the electric field to be transmitted from the electrodes on the paddle body (while inserted inside the introducer tool) to the target nerves. With the paddle body inserted into the introducer tool, this aperture is located on the side of the introducer tool that faces the paddle body when inserted into the introducer tool. In a curved introducer tool, this aperture is located on the concave side of the introducer tool.

In some embodiments, at least a portion of the introducer tool (e.g. portions that face the electrodes on the paddle body when inserted into the introducer tool) is made of a non-metallic material (for example, plastics such as silicone, polycarbonate, polypropylene, etc.) that allows permeation of the electric field from the electrodes through the introducer tool. In some embodiments, at least a portion of the introducer tool (e.g. portions that face the electrodes on the paddle body when inserted into the introducer tool) is sufficiently thin to allow penetration of the electric field from the electrodes. In some cases, such portions have a thickness of 2.5 mm or thinner; in some cases, a thickness of 2.0 mm or thinner; in some cases, a thickness of 1.5 mm or thinner. In a curved introducer tool, these non-metallic or thin portions may be located on the concave side of the introducer tool.

5. Example Method.

Figure 29A:
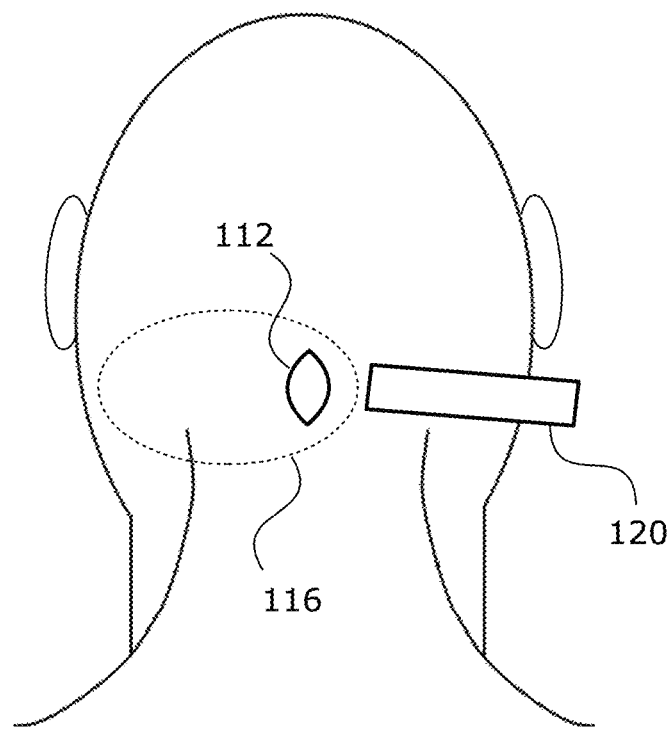
Figure 29B:
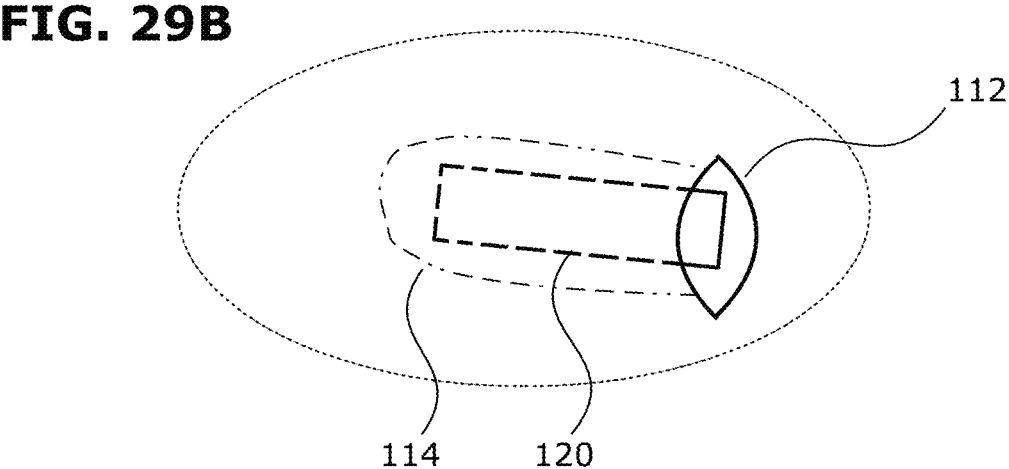

FIGS. 29A-F show an example method for implanting a paddle lead in the occipital region of the head/neck using an introducer tool of my invention. As shown in FIG. 29A, the surgeon makes a vertical midline incision 112 at a site on the posterior head/neck. The oval area 116 is shown in isolation in FIGS. 29B-E. As shown in FIG. 29B, from that incision site 112, the surgeon creates a transversely oriented subcutaneous tunnel 114 along the subcutaneous plane of the skin (e.g. using a blunt dissector tool). The introducer tool 120 is then inserted into the subcutaneous tunnel 114.

Alternatively, the introducer tool 120 itself can be used for making the subcutaneous tunnel 114 using the introducer tool 120 alone or in combination with other tools using any suitable surgical technique for creating subcutaneous tunnels. For example, an obturator or rigid stylet can be inserted into the hollow channel of introducer tool 120 and this tool combination can be used for tissue dissection to create subcutaneous tunnel 114. After the desired subcutaneous tunnel 114 is created, the obturator or stylet is then withdrawn from the introducer tool 120, leaving the introducer tool 120 within the subcutaneous tunnel 114.

As shown in FIG. 29C, the paddle body 124 of the paddle lead (with lead wire 126) is inserted into the hollow channel of the introducer tool 120. As shown in FIG. 29D, the paddle body 124 is advanced through the introducer tool 120 until it is positioned at the desired position. The position of the paddle body 124 and/or the introducer tool 120 may be adjusted to achieve optimal stimulation for the patient. This positioning may be facilitated by activating the paddle lead for electrical neurostimulation and observing the effectiveness of the neurostimulation. As shown in FIG. 29E, the introducer tool 120 is then withdrawn over the paddle body 124 and lead wire 126, leaving the paddle body 124 in the subcutaneous tunnel 114. The lead wire and implantable power source can be placed in a conventional manner.

In some embodiments, the clinician can further make a second incision at a second site on the posterior head/neck that overlies the distal end of the introducer tool 120 and/or paddle body 124 (e.g. to the left or right side of the first incision site 112). This may be useful for helping to adjust the position of the paddle body 124 and/or introducer tool 120. Also, this may be useful for anchoring the distal end of the paddle body 124 to the underlying fascia.

6. Summary.

In one embodiment, my invention can be described as an introducer tool used for inserting a paddle lead into a subcutaneous tunnel made in the craniofacial region (e.g. the posterior head/neck region). The introducer tool may have the dimensions and/or shape described above and/or other features as described above. The introducer tool may be designed to allow the electrodes on the paddle lead to operate while inside the introducer tool as described above. The introducer tool may be provided as part of a neurostimulator kit or set, such as a neurostimulator apparatus kit or neurostimulator implantation tool set.

In another embodiment, my invention is a method of implanting a paddle-type neurostimulation lead under the skin at a craniofacial site on the patient's body. The method comprises inserting the introducer tool under the skin at the target site and inserting the paddle body of the paddle lead into the hollow channel of the introducer tool. These steps can be performed in any order or combined as a single step. In some embodiments, the introducer tool is used to create a subcutaneous tunnel for the paddle lead. In some embodiments, electric field stimulation of the target nerve occurs while the paddle body is inside the introducer tool. In some embodiments, the method comprises, with the paddle body inside the introducer tool, activating the paddle lead for electrical neurostimulation and adjusting the position of the paddle body or the introducer tool according to the neurostimulation effect achieved.

In relevant embodiments of the introducer tool, the introducer tool may be deformed to conform to the patient's body contour. In relevant embodiments of the introducer tool, the introducer tool may be inserted under the skin with the concave side facing towards the patient's body. In relevant embodiments of the introducer tool, the introducer tool may be inserted under the skin with the aperture facing inwardly towards the patient's body. In relevant embodiments of the introducer tool, the introducer tool may be inserted under the skin with the non-metallic material portion facing towards the patient's body.

In relevant embodiments of the introducer tool, the introducer tool may be inserted under the skin with the thin-walled portion facing towards the patient's body. In relevant embodiments of the introducer tool, the paddle body may be inserted into the introducer tool with the electrodes facing towards the aperture on the introducer tool. In relevant embodiments of the introducer tool, the paddle body may be inserted into the introducer tool with the electrodes facing towards the non-metallic material portion on the introducer tool. In relevant embodiments of the introducer tool, the paddle body may be inserted into the introducer tool with the electrodes facing towards the thin-walled portion of the introducer tool.

In another embodiment, my invention can be described as a method for implanting a paddle lead into a subcutaneous tunnel in the craniofacial region (e.g. the posterior head/neck region). The method comprises cutting a skin incision at a site in the craniofacial region (e.g. the posterior head/neck region); creating a subcutaneous tunnel along the subcutaneous plane of the skin from the incision site; inserting an introducer tool having a hollow channel into the subcutaneous tunnel. The steps of creating the subcutaneous tunnel and inserting the introducer tool can be separate distinct steps (e.g. the subcutaneous tunnel is created by blunt dissection using a separate tool that is not the introducer tool) or it can be performed together (e.g. the subcutaneous tunnel is created by blunt dissection using an obturator inserted into the introducer tool, and after the subcutaneous tunnel is created, the obturator is then withdrawn from the introducer tool). The method further comprises: inserting a paddle body of a paddle lead into the hollow channel of the introducer tool; advancing the paddle body to the desired position; and withdrawing the introducer tool, leaving the paddle body within the subcutaneous tunnel. The method may further comprise, with the paddle body inside the introducer tool, activating the paddle lead for electrical neurostimulation and adjusting the position of the paddle body and/or the introducer tool according to the neurostimulation effect achieved.

The method may further comprise anchoring the paddle body to the body tissue (e.g. the fascia). In some cases, the paddle body is anchored somewhere at its proximal one-third section, but not the distal end of the paddle body. In some cases, the lead implantation method is performed without making another incision at a site near the distal end of the introducer tool. Alternatively, the method may further comprise cutting a second skin incision at a site near the distal end of the introducer tool. This may be helpful for positioning of the introducer tool and/or paddle body, or anchoring the paddle body to the fascia.

E. Ribbon Lead Wires (1-5 Below)

Another aspect of my invention is a lead wire that is designed for use in the craniofacial region. The lead wire contains the conductive electrode wires that power the electrodes on the paddle body. The electrically insulative material surrounding the conductive electrode wires inside the lead wire may be any flexible plastic or fabric material suitable for implantation in the body such as silicone, polyurethane, polyether ether ketone (PEEK), polyvinyl chloride (PVC), epoxy resin, etc. Many people have little soft tissue cushioning at their back of the head/neck. Because of this lack of cushioning, hardware implanted in this region can be uncomfortably palpable to the patient. This can also cause muscle soreness, skin irritation, or skin erosion. Lowering the profile of the lead wire can address this type of problem.

At least a portion of the lead wire has a ribbon configuration in which its height is one-third its width or less; in some cases, one-fifth its width or less. The entire length of the lead wire may be in a ribbon configuration or only a portion(s) thereof. The term "ribbon lead wire" as used herein does not necessarily mean that the entire length of the lead wire is in a ribbon configuration. The term "ribbon lead wire" is used to simplify the description herein and is intended to encompass lead wires having only a portion(s) that is in a ribbon configuration. Other portions of the lead wire can be in any other configuration, such as a conventional cylindrical (round) configuration or any other geometry in which its height is greater than one-third its width.

1. Dimensions.

In some embodiments, the height of the ribbon lead wire is one-fifth its width or less. In some embodiments, the ribbon lead wire has a thickness of 1.3 mm or less and has a width of 6 mm or greater. In some embodiments, the width of ribbon lead wire is in the range of 6-21 mm; and in some cases, in the range of 6-17 mm. In some embodiments, the ribbon lead wire is more flexible than the paddle body. In situations where it is difficult to separately distinguish the paddle body from its ribbon lead wire (e.g. it may be formed as a single continuous strip), my invention can be defined as the combined length of the paddle body and the ribbon lead wire being at least 7 cm long; in some cases, at least 13 cm long.

The full length of the ribbon lead wire does not necessarily have a ribbon configuration. In some embodiments, the ribbon lead wire further comprises a portion that does not have a ribbon configuration (i.e. its height is greater than one-third its width). In some cases, the portion of the ribbon lead wire that extends directly out from the paddle body has a ribbon configuration, and then proximal to this portion, another portion of the lead wire does not have a ribbon configuration. In some cases, this non-ribbon portion begins at a distance at least 7 cm from the paddle body; in some cases, beginning at a distance 7-25 cm from the paddle body. Distances from the paddle body are measured traveling along the length of the lead wire. This type of configuration can be useful for a lead wire that maintains a low profile in the head/neck region, but switches to a conventional lead wire configuration as it travels into the patient's upper back where the above-described problems may be less severe. In some cases, the ribbon configuration portion of the lead wire extends from the paddle body for at least a 2 cm length; in some cases, at least a 4 cm length.

Figure 30A:
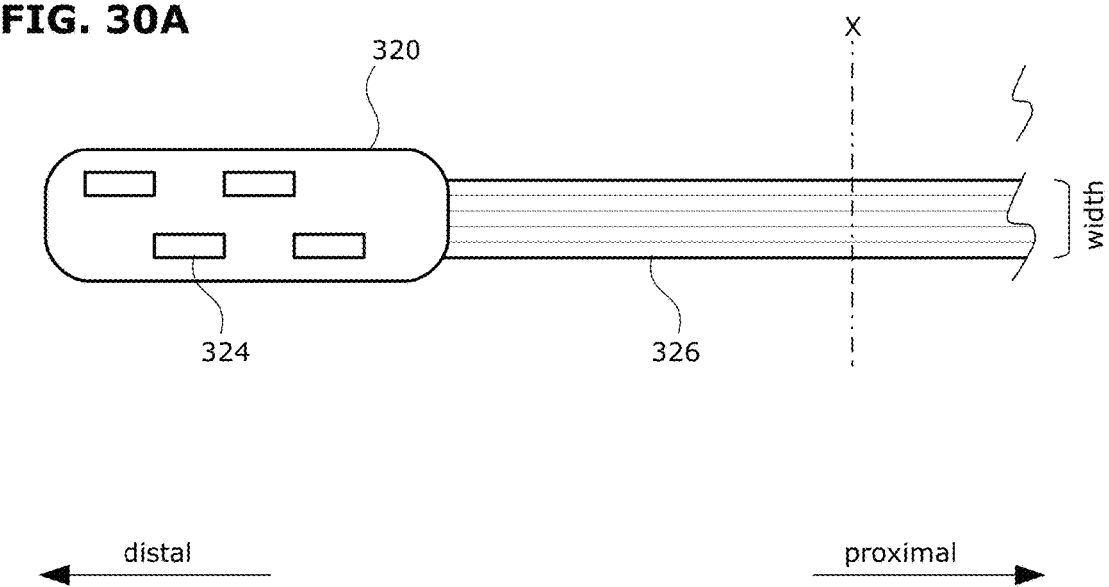
FIGS. 30A-B shows a paddle-type neurostimulation lead having a ribbon lead wire.
Figure 30B:
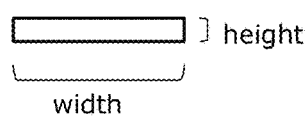

FIGS. 30A-B shows an example of a paddle-type neurostimulation lead according to my invention (with the distal and proximal directions indicated). As shown in FIG. 30A, the paddle-type neurostimulation lead comprises a paddle body 320 having electrodes 324 thereon. A ribbon lead wire 326 extends out from the paddle body 320. FIG. 30B shows the transverse cross-section view of the ribbon lead wire 326 at the dashed line "X" in FIG. 30A, and demonstrates the low profile characteristic of the ribbon lead wire.

2. Preset Bend.

In some embodiments, the ribbon lead wire has a preset bend in its path. This feature can be useful in accommodating the traction on the lead caused by movement in the head, neck, or upper body, thereby reducing the incidence of hardware breakage or lead migration. As used herein, the term "bend" in regards to the ribbon lead wire means a change in the direction of the path taken by the lead wire. The bend may also be characterized as being a curve, turn, arc, corner, angle, flexure, etc. As used herein, "bend angle" means the angle difference in the direction of the path taken by the lead wire after the bend as compared to the direction taken before the bend. This angle is measured with both direction vectors pointing away from the point of the bend. The bend angle is between 0-180°. In some embodiments, the bend angle ranges from 90° to 150°. This bend may occur abruptly (e.g. a sharp turn) or gradually (e.g. a curve), or any combination or continuum therebetween. In some embodiments, this bend occurs in the ribbon lead wire at a distance of 2-11 cm from the paddle body (along the path of the lead wire).

This bend is preset, i.e. it is "built into" the lead wire and takes on this configuration in the absence of any deforming force. However, the bend may still be flexible or elastic such that it can be forcibly deformed to take on other configurations. In some embodiments, the preset bend is elastically flexible. The term "elastically flexible" means that the bend in the lead wire is temporarily deformable to a new shape or size by human-applied force (e.g. bending, pulling, pushing, etc.) and returns substantially back to its original geometry when the force is removed. This feature can be useful in accommodating the traction on the lead wire caused by the movement in the head, neck, or upper body. In some embodiments, the bend is elastically flexible under the following testing procedure: change the bend angle by 30° (positive or negative) and then release the bending force. If the bend in the lead wire returns substantially to its original geometry after the deforming force is removed, then it would be considered "elastically flexible" for the purposes herein. This testing procedure description is not intended to limit the amount of elasticity in the bend and encompasses bends that are even more flexible than this (e.g. if is elastically flexible to −60° deformation, then it will certainly be elastically flexible to −30° deformation).

Figure 31A:
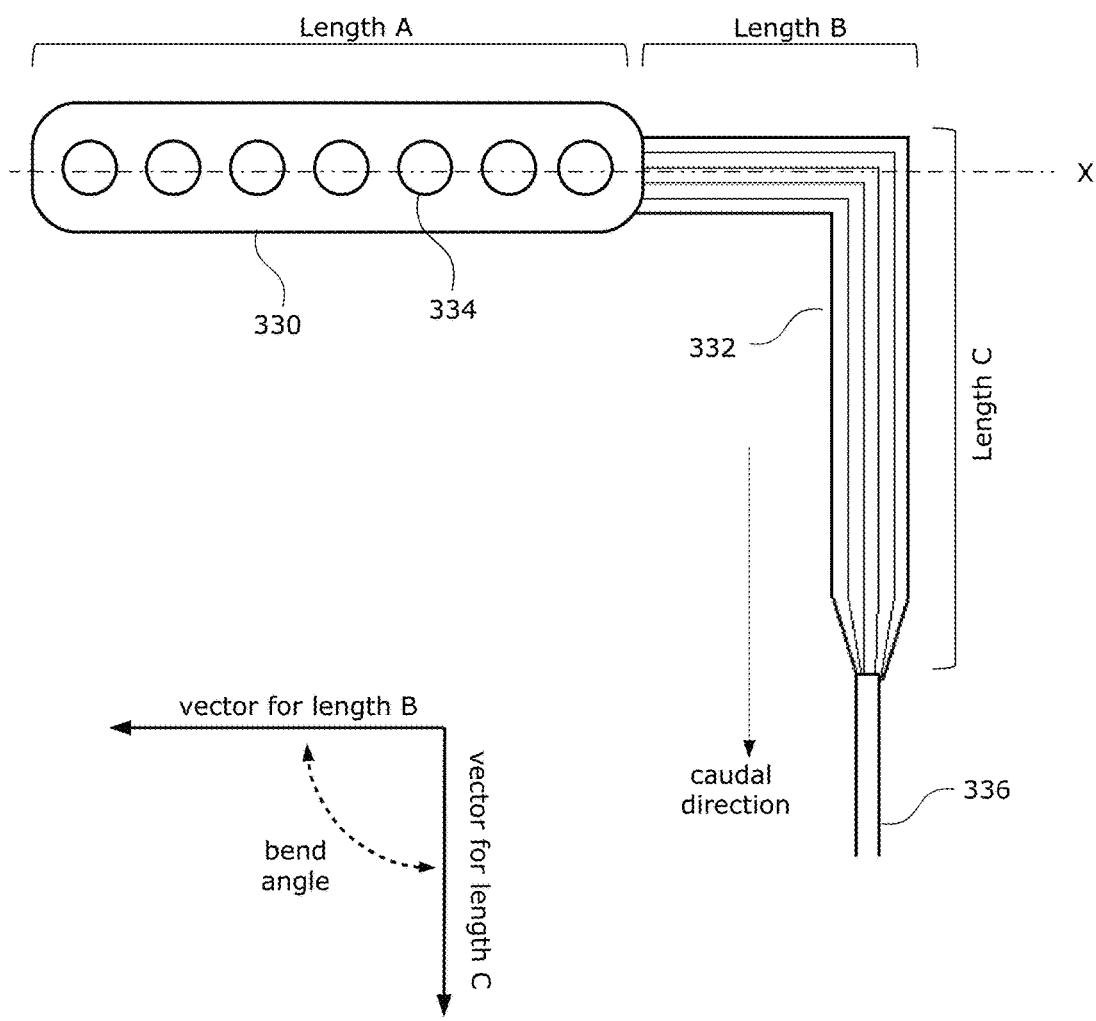
FIGS. 31A-C shows a paddle-type neurostimulation lead having a bended ribbon lead wire.
Figure 31B:
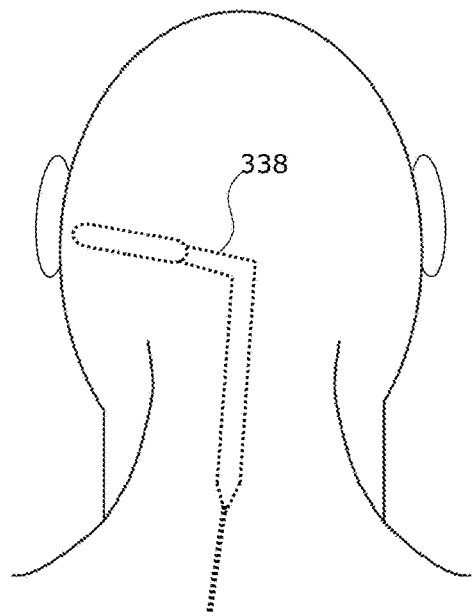
Figure 31C:
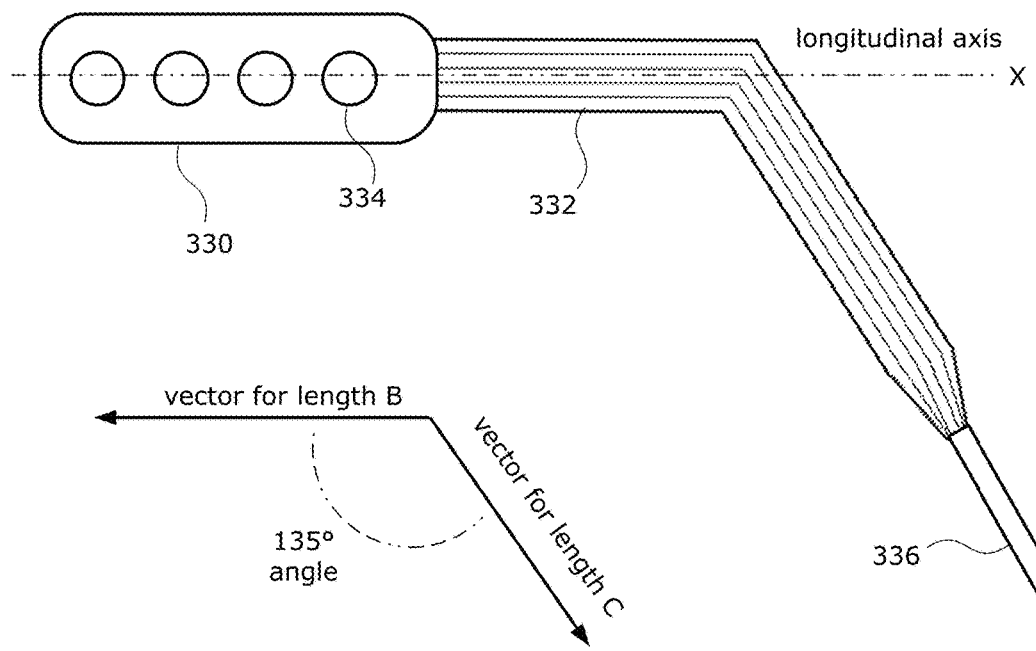

FIGS. 31A-C shows an example of a neurostimulation lead that implements features from several of the above-described embodiments in combination. FIG. 31A shows a paddle-type neurostimulation lead designed for implantation in the left side of the patient's posterior head/neck. The paddle body 330 has six electrodes 334 that are powered via conductive wires embedded in a ribbon lead wire, which has a ribbon configuration portion 332 extending out from the paddle body 330. The ribbon configuration portion 332 extends in the same direction as the longitudinal axis of the paddle body 330 for a distance of Length B. The lead wire then makes a 90° turn towards a caudal direction and continues for Length C in the new direction. At the proximal end of the ribbon configuration portion 332, the ribbon lead wire tapers and changes into a cylindrical (round) configuration 336. The length of the ribbon-configuration portion 332 is the combined Length B+C.

FIG. 31B shows the neurostimulation lead 338 as implanted in the patient's posterior head/neck and demonstrates how these dimensions and configuration conform to this particular patient's body. With the "L"-shaped configuration of the ribbon lead wire, the paddle body is oriented in a direction to cross over the greater occipital nerve, while allowing the lead wire to travel in a caudal direction as it descends down the back of the neck towards the patient's upper back region.

FIG. 31C shows how the bend in the ribbon lead wire can elastically deform when subject to pulling as the patient twists or turns their body. As seen here, the bend is oriented in a new direction of 135° (+45° relative to the original orientation of the bend). When the patient straightens her body, the deforming force is released and the ribbon-type lead wire returns back to its original geometry.

3. Fold-Over.

Figure 32A:
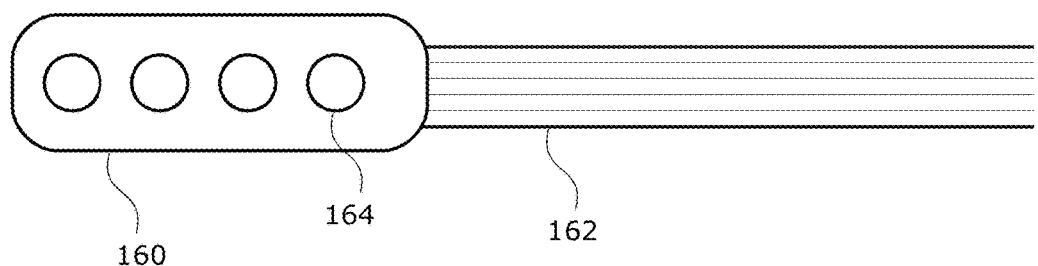
FIGS. 32A-B shows a paddle-type neurostimulation lead having a ribbon lead wire that can be folded over.
Figure 32B:
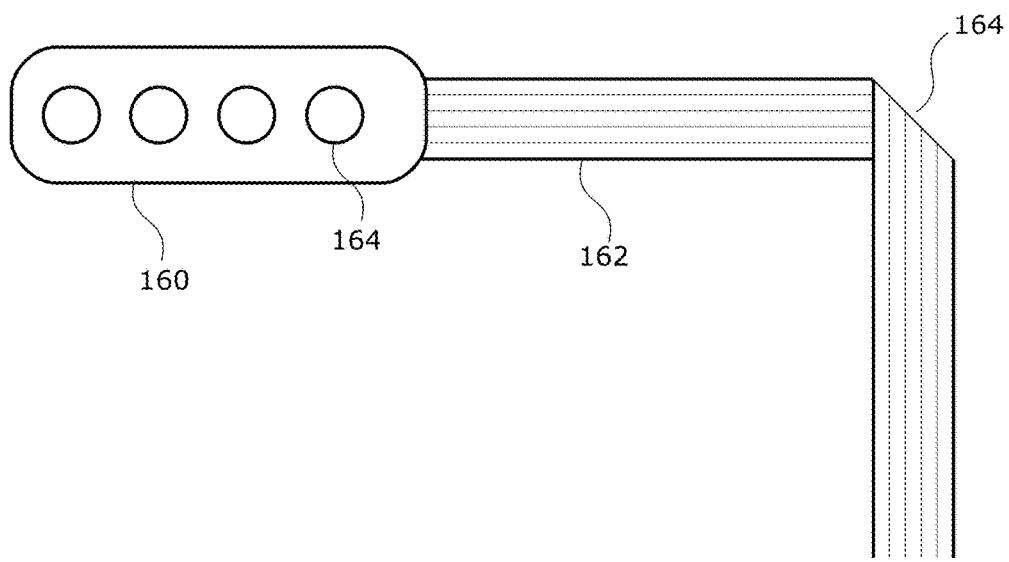

The ribbon-type lead wire can be sufficiently flexible and thin such that it can be folded over. As such, in some embodiments, the ribbon-type lead wire is folded over during implantation to switch the direction of the lead wire. FIGS. 32A-B shows an example of a neurostimulation lead according to my invention. As shown in FIG. 32A, the neurostimulation lead comprises a paddle body 160 having multiple electrodes 164 thereon. At its proximal end, the paddle body 160 is connected to a ribbon lead wire 162. As shown in FIG. 32B, the ribbon lead wire 162 is sufficiently thin that it can be folded over (at fold 164) to point in a caudal direction.

4. Suture Holding Feature.

There may be a suture holding feature attached to or built into the ribbon lead wire. As such, in some embodiments, the ribbon lead wire comprises a suture holding feature. This suture holding feature can be located anywhere along the length of the lead wire. In some embodiments, the suture holding feature is located within 10 cm of where the lead wire attaches to the paddle body (the 10 cm distance being measured along the travel path of the lead wire). In some embodiments, where the ribbon lead wire has a bend, the suture holding feature is at a location within 3 cm of the bend.

Figure 33:
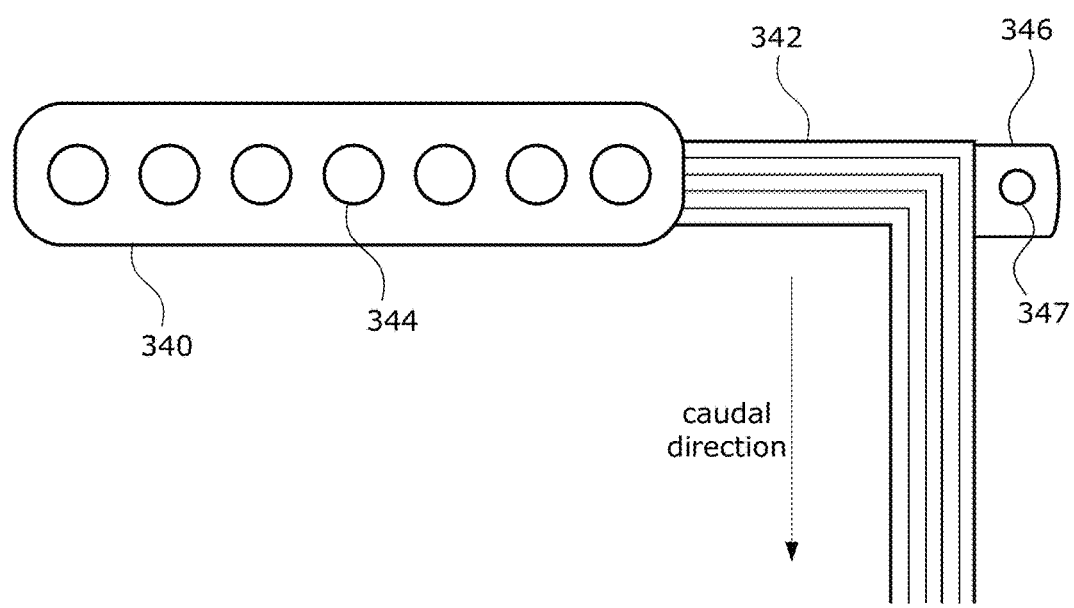
FIG. 33 shows a paddle-type neurostimulation lead having a ribbon lead wire with a suture tab.

FIG. 33 shows an example of a neurostimulation lead according to my invention. The neurostimulation lead comprises a paddle body 340 having multiple electrodes 344 thereon. At its proximal end, the paddle body 340 is connected to a ribbon lead wire 342, which has a 90° bend that reorients the lead wire in a caudal direction. At the location of the bend, there is a suture tab 346 attached to the ribbon lead wire 342. The suture tab 346 has a suture eyelet 347 for holding a suture that secures the ribbon lead wire to body tissue.

5. Summary.

In one embodiment, my invention can be described as a paddle-type neurostimulation lead that comprises a paddle body and a lead wire, with the lead wire being a ribbon lead wire as described above. In another embodiment, my invention is a method of treating a pain condition in a patient by implanting a paddle-type neurostimulation lead having a ribbon lead wire as described above. For relevant embodiments of the neurostimulation lead, the bend in the lead wire can be directed in the caudal direction. For relevant embodiments of the neurostimulation lead, the lead wire can be folded over; in some cases, the lead wire is folded over to point in a caudal direction; in some cases, the lead wire proximal to the fold is made to run caudally down the patient's neck. For relevant embodiments of the neurostimulation lead, the lead wire can be sutured to subcutaneous body tissue (e.g. fascia) at a point along the length of the lead wire; in some cases, the lead wire is sutured at a point 10 cm from where the lead wire attaches to the paddle body. In some embodiments, any suitable type of lead wire anchor can be applied onto the folded portion of the lead wire to help anchor the ribbon-type lead wire or maintain it in the folded-over configuration. For relevant embodiments of the neurostimulation lead, the lead wire can be sutured at a point that is 3 cm from the bend.

F. Conclusion

Within each of the sections A-E above, the features described therein can be combined with each other. Also, combinations between the embodiments described in sections A-E are possible. For example, the paddle lead and its methods of use can be combined with the lead wire anchor or selectable electrodes described herein. In another example, the neurostimulation lead with selectable electrodes can be used in combination with the curved paddle body or lead wire anchor described herein. In another example, the lead wire anchor can be used in combination with the neurostimulation apparatus or paddle lead described herein. In another example, the introducer tool can be used in combination with the neurostimulation apparatus or paddle lead described herein. In another example, the ribbon lead wire can be used in combination with the neurostimulation apparatus, lead wire anchor, or paddle lead described herein.

The foregoing description and examples have been set forth merely to illustrate my invention and are not intended to be limiting. Each of the disclosed aspects and embodiments of my invention may be considered individually or in combination with other aspects, embodiments, and variations of my invention. In addition, unless otherwise specified, the steps of the methods of my invention are not confined to any particular order of performance. Modifications of the disclosed embodiments incorporating the spirit and substance of my invention may occur to persons skilled in the art, and such modifications are within the scope of my invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

I claim:

1. In a patient with a neurostimulation lead implanted in the patient's craniofacial region,
    wherein the neurostimulation lead comprises a lead wire and a lead body having multiple electrodes,
    wherein the neurostimulation lead is coupled to a programmable power source,
    wherein the electrodes are individually selectable for activation and the power source is programmable to individually activate the electrodes,
    wherein a preadjustment set of one or more of the electrodes are selectively activated to stimulate a target nerve;
    a method of adjusting the neurostimulation being applied to the patient after the lead body has migrated in a medial and/or downward direction, the method comprising programming the power source to:
    (a) selectively deactivate the proximal-most electrode of the preadjustment set of activated electrodes; and
    (b) selectively activate a previously inactive electrode that is located distal to the preadjustment set of activated electrodes.

2. The method of claim 1, wherein the lead body is a cylindrical-type lead body.

3. The method of claim 2, wherein the deactivated electrode is an electrode that does not overlie the target nerve after lead migration has occurred.

4. The method of claim 3, wherein the craniofacial region is an occipital region of the patient's head and wherein the target nerve is an occipital nerve.

5. The method of claim 4, wherein the lead wire travels caudally down the patient's neck.

6. The method of claim 3, wherein the lead wire travels caudally down the patient's neck.

7. The method of claim 1, wherein the deactivated electrode is an electrode that does not overlie the target nerve after lead migration has occurred.

8. The method of claim 7, wherein the craniofacial region is an occipital region of the patient's head and wherein the target nerve is an occipital nerve.

9. The method of claim 8, wherein the lead wire travels caudally down the patient's neck.

10. The method of claim 7, wherein the lead wire travels caudally down the patient's neck.

11. The method of claim 1, wherein the lead body is a paddle-type lead body.

12. The method of claim 11, wherein the paddle-type lead body has a longitudinal axis and a plane; and wherein the lead wire is connected to the paddle-type lead body and extends out at an angle relative to the longitudinal axis of the paddle-type lead body along the plane of the paddle-type lead body.

13. The method of claim 12, wherein the paddle-type lead body has a distal one-third section, a middle one-third section, and a proximal one-third section; wherein the lead wire connects to the paddle-type lead body at a point in the middle one-third section or proximal one-third section of the paddle-type lead body.

14. The method of claim 11, wherein the lead wire extends out from the paddle-type lead body at an angle in the range of 90° to 150° relative to the longitudinal axis of the paddle-type lead body.

15. The method of claim 11, wherein the lead wire connects to the paddle-type lead body at a proximal end of the paddle-type lead body.

16. The method of claim 11, wherein the lead wire connects to the paddle-type lead body at a lateral side of the paddle-type lead body.

17. The method of claim 1, wherein the craniofacial region is an occipital region of the patient's head and wherein the target nerve is an occipital nerve.

18. The method of claim 17, wherein the lead wire travels caudally down the patient's neck.

19. The method of claim 1, wherein the lead wire travels caudally down the patient's neck.

20. The method of claim 19, wherein the craniofacial region is an occipital region of the patient's head and wherein the target nerve is an occipital nerve.

* * * * *